United States Patent
Velliquette et al.

(10) Patent No.: US 10,532,024 B2
(45) Date of Patent: Jan. 14, 2020

(54) **TOPICAL COMPOSITIONS OF *LITHOSPERMUM ERYTHRORHIZON* (GROMWELL ROOT) FOR TREATING OR CONTROLLING EXCESSIVE OIL PRODUCTION IN SKIN AND MINIMIZING GLYCATION IN SKIN, AND METHODS OF USING THE COMPOSITIONS**

(71) Applicant: Access Business Group International LLC, Ada, MI (US)

(72) Inventors: Rodney A. Velliquette, Ada, MI (US); Kelly M. Glynn, Grand Rapids, MI (US); Ernest H. Brumbaugh, Grayling, MI (US); Penelope M. Anderson, Ada, MI (US); John F. Rebhun, Greenville, MI (US); Stephen R. Missler, Grand Rapids, MI (US); Arun Rajgopal, Grand Rapids, MI (US)

(73) Assignee: ACCESS BUSINESS GROUP INTERNATIONAL LLC, Ada, MI (US)

( * ) Notice: Subject to any disclaimer, the term of this patent is extended or adjusted under 35 U.S.C. 154(b) by 73 days.

(21) Appl. No.: 15/791,913

(22) Filed: Oct. 24, 2017

(65) Prior Publication Data
US 2018/0110722 A1 Apr. 26, 2018

Related U.S. Application Data

(60) Provisional application No. 62/412,608, filed on Oct. 25, 2016.

(51) Int. Cl.
| | |
|---|---|
| *A61K 36/30* | (2006.01) |
| *A61K 8/9789* | (2017.01) |
| *A61K 8/35* | (2006.01) |
| *A61K 31/122* | (2006.01) |
| *A61K 8/06* | (2006.01) |
| *A61K 9/107* | (2006.01) |
| *A61K 47/14* | (2017.01) |
| *A61K 8/37* | (2006.01) |
| *A61K 47/22* | (2006.01) |
| *A61K 8/49* | (2006.01) |
| *A61Q 19/08* | (2006.01) |
| *A61Q 19/00* | (2006.01) |
| *A61Q 17/04* | (2006.01) |
| *A61Q 5/12* | (2006.01) |
| *A61Q 1/04* | (2006.01) |
| *A61K 8/67* | (2006.01) |
| *A61Q 1/02* | (2006.01) |
| *A61K 9/00* | (2006.01) |
| *A61K 47/44* | (2017.01) |

(52) U.S. Cl.
CPC ............ *A61K 8/9789* (2017.08); *A61K 8/062* (2013.01); *A61K 8/064* (2013.01); *A61K 8/355* (2013.01); *A61K 8/37* (2013.01); *A61K 8/498* (2013.01); *A61K 8/678* (2013.01); *A61K 9/0014* (2013.01); *A61K 9/107* (2013.01); *A61K 31/122* (2013.01); *A61K 36/30* (2013.01); *A61K 47/14* (2013.01); *A61K 47/22* (2013.01); *A61K 47/44* (2013.01); *A61Q 1/02* (2013.01); *A61Q 1/04* (2013.01); *A61Q 5/12* (2013.01); *A61Q 17/04* (2013.01); *A61Q 19/00* (2013.01); *A61Q 19/008* (2013.01); *A61Q 19/08* (2013.01); *A61K 2236/35* (2013.01)

(58) Field of Classification Search
None
See application file for complete search history.

(56) References Cited

U.S. PATENT DOCUMENTS

| | | | |
|---|---|---|---|
| 6,184,274 B1 | 2/2001 | Schneider | |
| 6,419,962 B1 | 7/2002 | Yokoyama et al. | |
| 6,645,514 B1 | 11/2003 | Schneider et al. | |
| 2008/0081082 A1 | 4/2008 | Zimmerman et al. | |
| 2009/0269395 A1 | 10/2009 | Lintner et al. | |
| 2010/0158824 A1 | 6/2010 | Lin | |
| 2012/0258059 A1* | 10/2012 | Iwama | A61K 8/64 424/59 |
| 2013/0109756 A1* | 5/2013 | Huber | A61K 9/06 514/570 |
| 2014/0113976 A1 | 4/2014 | Matsumoto et al. | |
| 2017/0042784 A1* | 2/2017 | Munk | A61K 8/416 |
| 2018/0193244 A1* | 7/2018 | Hood | A61K 8/49 |

FOREIGN PATENT DOCUMENTS

| | | | |
|---|---|---|---|
| CN | 1895663 A | * | 1/2007 |
| KR | 2007102630 A | * | 10/2007 |

OTHER PUBLICATIONS

Chang M. et al. Cosmetic Formulations Containing Lithospermum erythrorhizon Root Extract Show Moisturizing Effects on Human Skin. Archives of Dermatologic Research 300(6)317-323, Jul. 2008. (Year: 2008).*

(Continued)

*Primary Examiner* — Ralph J Gitomer
(74) *Attorney, Agent, or Firm* — Brinks Gilson & Lione

(57) ABSTRACT

Compositions for suppressing sebum production in skin (e.g., seborrheic skin), and minimizing glycation in skin (e.g., mature skin) with enhanced UV absorptive properties are described. In particular, the present invention relates to a composition containing a skin benefit agent that includes *Lithospermum erythrorhizon*. Also, methods of suppressing sebum production in skin (e.g., seborrheic skin) and minimizing glycation in skin (e.g., mature skin) by applying a composition to the skin, wherein the composition comprises an effective amount of a derivative of *Lithospermum erythrorhizon* are also described.

22 Claims, 17 Drawing Sheets
(15 of 17 Drawing Sheet(s) Filed in Color)

(56) References Cited

OTHER PUBLICATIONS

Thiboutot D, et al., "Human Skin is a Steroidogenic Tissue: Steroidogenic Enzymes and Cofactors Are Expressed in Epidermis, Normal Sebocytes, and an Immortalized Sebocyte Cell Line (SEB-1)," *J Invest Dermatol.* 120:905-14 (2003).
The International Search Report And The Written Opinion Of The International Searching Authority received in PCT Application No. PCT/US2017/57887 dated Jan. 30, 2018.
Papageorgiou, V.P., et al., "The Chemistry and Biology of Alkannin, Shikonin, and Related Naphthazarin Natural Products," *Angew. Chem. Int. Ed.*, 38:270-300 (1999).
Assimopoulou, A.N. & Papageorgiou, V.P., "Radical Scavenging Activity of *Alkanna tinctoria* Root Extracts and their Main Constituents, Hydroxynaphthoquinones," *Phytother Res.*, 19:141-147 (2005).
Huang, Z.-S., et al., "Synthesis and cytotoxicity study of alkannin derivatives," *European Journal of Medicinal Chemistry*, 39:755-764 (2004).
Notification Concerning Transmittal of International Preliminary Report on Patentability dated May 9, 2019 including International Preliminary Report and Written Opinion of the International Searching Authority received in PCT Application No. PCT/US17/057887 dated Apr. 30, 2019.

* cited by examiner

**pH Titration Triggers Color Change/Isomerization.
pH triggered isomerization of Gromwell Root 0.10% (0.50%
FLAVEX in Adipate) in Water-Si Chassis activated by
combination with acid gel**

$R_1$: OH, $R_2$: H  Shikonin
$R_1$: H, $R_2$: OH  Alkannin

Water-in-Silicone Emulsion Microstructure

Oil-Free Facial Mattifier Stability: 2.5 Months @ Ambient Conditions and at 50°C A. Ambient     B. 2.5 months @ T=50°C ANTIOXIDANT STABILIZED    Exaggeration of isomerization followed by subsequent polymerization utilizing UV and surface catalytic phenomenon for transformation

Oil-in-Water Emulsion Microstructure

Medicated Anti-Blemish Treatment: 3 Months @ 50°C 3 months @ T=50°C      Ambient

Comparison of Shikonin & Alkannin Molecular Structures

Shikonin (C16H16O5)
288.3

Isobutylrylshikonin (C20H22O6)
358.4

Acetyl Shikonin (C18H18O6)
330.3

β,β-Dimethylacryl alkannin
(C21H22O6)
370.4

Deoxyshikonin (C16H16O4)
272.3

Isovalerylalkannin (C21H24O6)
372.4

Gromwell Root "Shades of Pink" Topical Application Prototypes

Gromwell Root extract 0.10% (0.50% FLAVEX in Adipate) in detergent testing complexes with caustic inducing cotton shirt staining

*1 µg/mL = 0.0001%

Based on this data, gromwell root extract would have 50% maximal efficacy at 0.0073% inclusion.

| P1, P2, and P3 Skin immersed in 0.10% Cheek Jelly for 21 hours at T=32°C water bath | P4, P5, and P6 Skin Transferred for 1 hour to Cheek Jelly BASE at T=32°C | P7, P8, and P9 Skin Transferred for 4 hours to Cheek Jelly BASE at T=32°C |

Progression of Skin Adsorption

Skin Tissue Adsorption Microscopy:
36 hours after immersion in Cheek Jelly.

Cheek Jelly Skin Tissue Adsorption Microscopy
40X Magnification of P10 tissue

Cheek Jelly Skin Tissue Adsorption Microscopy
10X Magnification of P10 tissue Lip & Cheek Jelly Prototype Physical Stability
ARTISTRY Contouring Lip & Cheek Jelly Prototype

Six Months 40C Gromwell Facial Mattifier

TOPICAL COMPOSITIONS OF *LITHOSPERMUM ERYTHRORHIZON* (GROMWELL ROOT) FOR TREATING OR CONTROLLING EXCESSIVE OIL PRODUCTION IN SKIN AND MINIMIZING GLYCATION IN SKIN, AND METHODS OF USING THE COMPOSITIONS

RELATED APPLICATIONS

The present patent document claims the benefit of the filing date under 35 U.S.C. § 119(e) of Provisional U.S. Patent Application Ser. No. 62/412,608, filed Oct. 25, 2016, which is hereby incorporated by reference.

BACKGROUND

The present invention relates to a treatment or control of oil production in skin; i.e., oily skin. Specifically, compositions for suppressing sebum production in skin (e.g., seborrheic skin) and minimizing glycation in skin (e.g., mature skin) are described. In particular, the present invention relates to a composition containing a skin benefit agent that includes *Lithospermum erythrorhizon*. Also, methods of suppressing sebum production in skin (e.g., seborrheic skin) and minimizing glycation in skin (e.g., mature skin) by applying a composition to the skin, wherein the composition comprises an effective amount of a derivative of *Lithospermum erythrorhizon* are also described.

The skin is rich in sebaceous glands and is continually renewed. The secretion of sebum is a normal phenomenon that is useful to both the skin and the head of hair. It is a natural product of the sebaceous gland, which is an annex of the pilosebaceous unit. It is, essentially, a more or less complex mixture of lipids. Sebum's normal function is to moisturize the epidermis. Also, sebum protects the skin and the scalp and gives the hair sheen by lubricating hair cuticles.

Unfortunately, a hypersecretion of sebum, or seborrhea, may lead to aesthetic disorders. Thus, an excessive secretion of sebum may result in oily skin with a shiny or glistening appearance. Hypersecretion of sebum may also promote the appearance of an oily dandruff condition of the scalp or oily dandruff. Oily skin, or seborrhea, is estimated to represent greater than 10% of younger populations (& >25% in China) within industrialized societies. Although sebum provides a very low level of UV absorptive function and moisturization, excessive oil production can foster a breeding ground for bacteria proliferation, clogged/enlarged pores, irritation and formation of acne lesions. It may be accompanied by an increase in pore size. For example, psychological stress, fatigue, onset of adolescence, hormonal fluctuations, sleep deprivation, high glycemic diet, and high humidity environments may be factors that intensify these conditions in the majority of people. Among the population having oily skin, some subjects may have endocrine disorders, acne vulgaris, or neurological disorders, or are obese. It is also possible to find adolescents, people suffering from excess hormones (in particular male hormones—androgens), menstruating women or menopausal women who have oily skin.

Also, in some conditions, such as, e.g., dermatosis (including seborrheic dermatitis), oily areas of the body, such as the face, upper chest and back are affected. More specifically, seborrheic dermatitis is a common, chronic, relapsing disease or condition of the skin presenting with dry or greasy scaling of the scalp, hairline, forehead, chin, nose, upper cheeks and nasolabial folds, sometimes accompanied by itching. In more severe cases, yellowish to reddish scaly pimples appear along the hairline, behind the ears, in the ear canal, on the eyebrows, on the bridge of the nose, around the nose, on the chest, and on the upper back. Seborrheic dermatitis can also be referred to as "seborrheic eczema" or "seborrhea." Typically, seborrheic dermatitis presents with scaly, flaky, itchy, and red skin. It particularly affects the anatomical sites of the skin in which sebaceous glands are dominant, such as scalp, face, chest, back, and ears. In adolescents and adults, seborrheic dermatitis usually presents as scalp scaling or as redness of the nasolabial fold.

As people age, proteins in the body can become damaged through the introduction of advanced glycation end products (AGEs)—one of the key factors in aging of the skin. The more sugar a person eats, whether processed or natural, the more AGEs are produced. The proteins in skin most prone to glycation are the same ones that make a youthful complexion so plump and springy—collagen and elastin. When those proteins hook up with renegade sugars, they become discolored, weak, and less supple; this shows up on the skin's surface as wrinkles, sagginess, and a loss of radiance. The presence of AGEs also makes the complexion more vulnerable to bad-news assailants such as UV light and cigarette smoke. When the body is overwhelmed with AGEs, collagen becomes compromised. Effects of the glycation process at the cellular level of the skin's structure may result in wrinkling, loss of elasticity, loss of volume, stiffness, accelerated aging and compromised barrier function. Other conditions that appear when microcirculation is damaged and cell turnover slows include a loss of volume in the face (particularly under eyes and lips) due to redistribution of fat.

Topical sun protection is one of the most important steps that consumers can take to prevent the premature signs of aging on the skin. With the massive shortage of globally compliant UV filters, and more particularly UV A—higher wavelength actives), the cosmetic industry is in dire need for better technology with UV absorptive and/or boosting function.

Therefore, a need exists to overcome these problems by providing compositions and methods for treating oily skin, conditions associated with oily skin, and facial applications providing the additional benefit of minimizing glycation in mature skin. Moreover, additional topical skincare applications leveraging natural colorants that target facial sites which are anatomically thinner such as periorbital, eyelid or lip care treatments are desired by the cosmetic industry at large. These anatomical sites often present with higher sensitivity, dehydration, loss of volume and early, visible signs of aging.

SUMMARY

One embodiment relates to a topical composition comprising a therapeutically effective amount of *Lithospermum erythrorhizon*; a lipophilic solubilizer; and a free radical stabilizer. The composition may comprise a therapeutically effective amount of an extract of *Lithospermum erythrorhizon* comprising shikonin compound(s), the lipophilic solubilizer and the free radical stabilizer being capable of inhibiting polymerization of the shikonin compounds, when in composition. The composition may be a water-in-silicone emulsion or an oil-in-water emulsion. The lipophilic solubilizer may be a non-comedogenic ester selected from the group consisting of adipates, caprylates, isononanoates, and select ethoxylated triglycerides. The non-comedogenic ester may be diisobutyl adipate. The free radical stabilizer may be a lipophilic antioxidant selected from the group consisting of tocols, carotenoids, and phenolics. The lipophilic antioxidant may be tocopherol. The composition may be for suppressing sebum production in a subject with dermatosis. The composition may be for minimizing glycation in mature skin. The composition may further comprise a pharmaceutically acceptable carrier, wherein the composition may have a pH from about 4.0 to about 8.0. The composition may be an oil-free composition. The composition may be in a form of cream, lotion, pack or powder, emulsion, liniment foam, plaster, granules, or ointment. The composition may be an over-the-counter drug composition, pharmaceutical composition, Japanese/Korean quasi-drug, Chinese special-use cosmetic composition or global cosmetic composition.

Another embodiment relates to a method for treating oily skin associated with dermatosis in a subject in need thereof comprising applying to an affected area of the subject a therapeutically-effective amount of the described composition. The dermatosis may be seborrheic dermatitis. The subject may present with desquamation, erythema, pruritus, inflammation, lichenification, excoriation, stinging, scaling, or increased sebum production. The affected area may be the scalp, including the hairline, ear canals, or behind the ears; the face, including the eyebrows, nose, or nasolabial folds; and the trunk, including the chest or back. The composition may be applied once daily, twice daily, or as needed.

Another embodiment relates to a method for minimizing glycation in mature skin in a subject in need of the treatment comprising applying to the subject the described composition. The composition may be applied once daily, twice daily, or as needed. The subject may present with wrinkling, sagginess, loss of radiance, loss of skin elasticity, skin stiffness, normal or accelerated skin aging, compromised skin barrier function, or loss of volume in the face (under eyes or lips) due to redistribution of fat or other skin-aging characteristics.

Yet another embodiment relates to a method for reducing or preventing advanced glycation end products (AGEs) in skin of a human subject in need of the treatment comprising applying to the subject the described composition.

BRIEF DESCRIPTION OF THE DRAWINGS

The patent or application file contains at least one drawing (color photographs) executed in color. Copies of this patent or patent application publication with color drawing(s) will be provided by the Office upon request and payment of the necessary fee.

DETAILED DESCRIPTION OF THE DRAWINGS AND THE PRESENTLY PREFERRED EMBODIMENTS

Figure 1:
FIG. 1 shows: (A) a photograph demonstrating that pH titration triggers color change/polymerization. pH triggered polymerization of gromwell root extract 0.10% (0.50% FLAVEX in adipate) in water-in-silicone (W/Si) chassis activated by combination with acid gel; and (B) chemical structures of the isomers of gromwell root.
Figure 1:
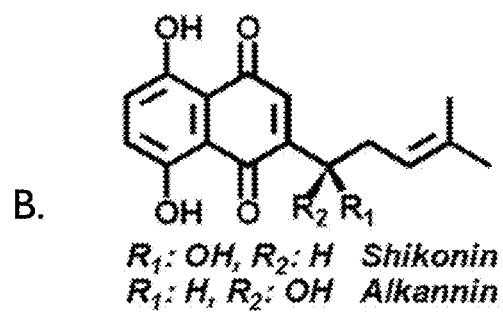

There is an unmet need for topical products to provide immediate coverage of skin imperfections combined with sustained biological efficacy. Gromwell root uniquely provides natural coloration to immediately neutralize skin imperfections such as sallowness, yellowing, lack of pigmentation, or hyperpigmentation in a topical multifunctional vehicle.

It is to be understood that this invention is not limited to the particular compositions, methodology, or protocols described herein. Further, unless defined otherwise, all technical and scientific terms used herein have the same meaning as commonly understood to one of ordinary skill in the art to which this invention belongs. It is also to be understood that the terminology used herein is for the purpose of describing particular embodiments only, and is not intended to limit the scope of the present invention, which will be limited only by the claims.

Described are topical formulations including *Lithospermum erythrorhizon* ("gromwell root"), a natural colorant, for immediate and long term skin and hair health benefits. The formulations may be water-in-oil, oil-in-water, or hydroalcoholic gel formulations.

The present invention is based on the surprising discovery, through cellular testing, that the gromwell root extract can suppress sterol regulatory element-binding protein 1c (SRBEP1c) and immortalized human sebaceous gland cell line (SEB-1) sebum production and proliferation. Formulating gromwell root extract into a composition for use in various skin applications, however, requires proper solubilization and stabilization, and prevention of polymerization to maximize skin permeation and avoid photocatalytic transition (from light, heat, singlet oxygen/hydroxyl/free radical, electrolytic exposure). It was discovered that incorporating non-comedogenic esters (such as adipates, caprylates, isononanoates, and some ethoxylated triglycerides) with lipophilic antioxidants into the composition with gromwell root extract may be beneficial for inhibition of polymerization of shikonin napthoquinones of gromwell root extract allowing for formulating into described compositions. Low molecular weight hydrocarbons such as hydrogenated polyisobutene, mineral oil, and chemical UV filters such as octyl salicylate, Octinoxate, octocrylene, and butyl octyl salicylate or Ethylhexyl methoxycrylene (UV boosters), or natural oils (argan oil, soybean oil, safflower oil, etc.) can also be used to solubilize gromwell extract. The demonstrated stabilization of gromwell root extract also resolves the gromwell root extract's innate tendency to polymerize into larger molecular weight nathoquinones (adduct moieties), which impede solubility and subsequent skin penetration.

Formulations comprised of gromwell root extract, tocopherol and adipate are also described for suppressing sebum production in skin (e.g., in seborrheic skin) and minimizing glycation in mature skin.

Although gromwell root extract has been used sparingly in the cosmetic industry as a colorant/dye or in ointments, combined with other ingredients, for skin burns and psoriasis, the previously described formulations are dramatically different in composition and function and do not include a properly solubilized and stabilized gromwell root extract, as shown for the described compositions.

Definitions

The terms "composition" or "formulation" refer to a product that treats, improves, promotes, increases, manages, controls, maintains, optimizes, modifies, reduces, inhibits, or prevents a particular condition associated with a natural state, biological process or disease or disorder. For example, a composition or a formulation improves at least one sign of oily skin in a subject, especially as presented in seborrheic dermatitis, and/or minimizes glycation in skin (e.g., mature skin). The terms composition and formulation include, but are not limited to, pharmaceutical (i.e., drug), over-the-counter (OTC), cosmetic, food, food ingredient or dietary supplement compositions that include an effective amount of an extract, at least one component thereof, or a mixture thereof. Exemplary compositions and/or formulations include cream, cosmetic lotion, pack or powder, or as an emulsion, lotion, liniment foam, tablets, plasters, granules, or ointment. Preferred compositions are formulated for topical application/administration.

As used herein, the term "extract" or "botanical extract" refers to a solid, viscid, or liquid substance or preparation that includes an active ingredient(s) of a substance of plant, *Lithospermum erythrorhizon*. The term "extract" is intended to include not only a crude extract produced from *Lithospermum erythrorhizon*, and by use of a $CO_2$ extraction method and secondary extraction with diisobutyl adipate via countercurrent liquid-liquid technique; but also a fraction of the crude extract prepared by the same extraction method and/or a pure compound, composition, extract mixture, component of the extract, and/or active agent or ingredient, or a combination thereof. One example of a botanical extract includes an extract from *Lithospermum* (*Lithospermum erythrorhizon*).

As used herein, the term "effective amount" or "therapeutically effective amount" of a pure compound, composition, extract, extract mixture, component of the extract, and/or active agent or ingredient, or a combination thereof refers to an amount effective at dosages and for periods of time sufficient to achieve a desired result. For example, the "effective amount" or "therapeutically effective amount" refers to that amount of a pure compound, composition, extract, botanical extract, extract mixture, botanical extract mixture, component of the extract, and/or active agent or ingredient, or a combination thereof of this invention which, when administered to a subject (e.g., mammal, such as a human), is sufficient to effect treatment, such as improving oily skin by suppressing sebum production in seborrheic skin and/or minimizing glycation in mature skin, as well as UV absorptive and/or boosting function (i.e., helping provide supplemental UV protection in cosmetic products). The amount of a composition, extract, botanical extract, extract mixture, botanical extract mixture, component of the extract, and/or active agent or ingredient of this disclosure that constitutes an "effective amount" or "therapeutically effective treatment" will vary depending on the active agent or the compound, the condition being treated and its severity, the manner of administration, the duration of treatment, or the age of the subject to be treated, but can be determined routinely by one of ordinary skill in the art having regard to his own knowledge and to this disclosure.

The term "pharmaceutically acceptable" means those drugs, medicaments, extracts or inert ingredients, which are suitable for use in contact with the tissues of humans and lower animals without undue toxicity, incompatibility, instability, irritation, and the like, commensurate with a reasonable benefit/risk ratio.

The terms "applying" and "administering" are defined as providing a composition to a subject via a route known in the art, including but not limited to topical, intravenous, intraarterial, oral, parenteral, buccal, transdermal, rectal, intramuscular, subcutaneous, intraosseous, transmucosal, or intraperitoneal routes of administration. In preferred embodiments, topical routes of administering the described composition are suitable.

The term "seborrheic skin" refers to a subject's skin having or experiencing a common, chronic, relapsing skin condition that affects scalp, face and torso, referred to as "seborrheic dermatitis," "seborrheic eczema" or "seborrhea." Seborrheic dermatitis causes scaly, flaky, itchy patches, red skin and stubborn dandruff. Seborrheic dermatitis can also affect oily areas of the body, such as the face, upper chest and back. Typically, seborrheic dermatitis presents with scaly, flaky, itchy, and red skin. It particularly affects the sebaceous-gland-rich areas of skin. In adolescents and adults, seborrheic dermatitis usually presents as scalp scaling or as redness of the nasolabial fold. Excessive sebum production in the skin is also one of the key causative factors of acne vulgaris, a skin disorder impacting ~85% of adolescents or young urban dwellers in industrialized societies.

The terms "minimize," "reduce," "suppress," "decrease" and/or "inhibit" refer to a decrease or reduction in protein activity and/or expression, and/or its downstream effect, in the presence of a plant ingredient or plant extract of *Lithospermum erythrorhizon*, when compared to protein activity and/or expression in the absence of a plant ingredient or plant extract of *Lithospermum erythrorhizon*, such as in a control sample. The degree of decrease or inhibition of protein activity and/or expression, and/or its downstream effect, will vary with the nature and quantity of a plant ingredient or plant extract of *Lithospermum erythrorhizon* present, but will be evident, e.g., as a detectable decrease in protein activity and/or expression; desirably a degree of decrease greater than about 5%, about 10%, about 15%, about 20%, about 25%, about 50%, about 75%, about 90%, about 95% or about 99% (or any degree of decrease in the range of from about 5% to about 99%) as compared to protein activity and/or expression in the absence of *Lithospermum erythrorhizon*. For example, a composition comprising a plant ingredient or plant extract of *Lithospermum erythrorhizon* can suppress or reduce sebum production in skin, such as seborrheic skin. In another example, a composition comprising a plant ingredient or plant extract of *Lithospermum erythrorhizon* can minimize or reduce glycation in skin, such as a mature skin.

As used herein, the term "subject" or "individual" includes mammals to which a composition may be administered. Non-limiting examples of mammals include humans, non-human primates, rodents (including transgenic and non-transgenic mice) or the like. In some embodiments, the subject is a mammal, and in some embodiments, the subject is human.

Compositions

In certain embodiments, water-in-silicone compositions are described.

In certain other embodiments, oil-in-water compositions are described.

In certain embodiments, the compositions are oil-free compositions.

In certain embodiments, the described compositions are topical compositions comprising a therapeutically effective amount of *Lithospermum erythrorhizon*; a lipophilic solubilizer (e.g., a non-comedogenic ester), and a free radical stabilizer (e.g., a lipophilic antioxidant).

In certain embodiments, the topical compositions are suitable for the management of sebum production or oily skin in dermatosis, such as seborrheic dermatitis, and/or minimizing glycation in skin (e.g., mature skin).

Figure 10:
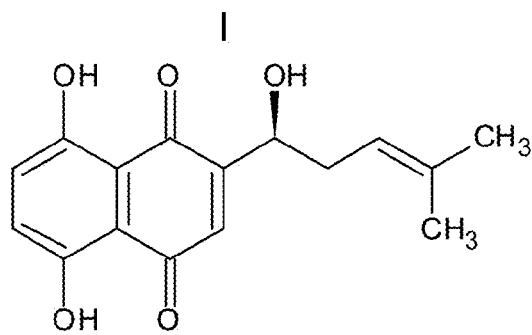
FIG. 10 depicts molecular structures of shikonin and alkanin naphthoquinones of gromwell root.
Figure 10:
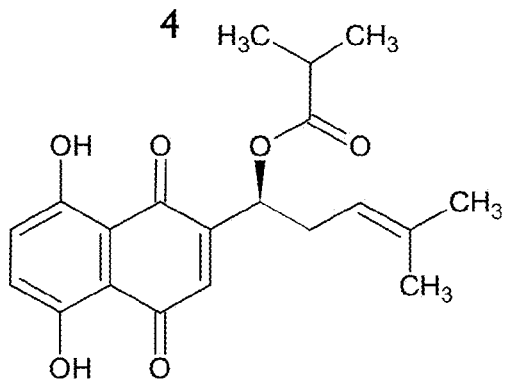
Figure 10:
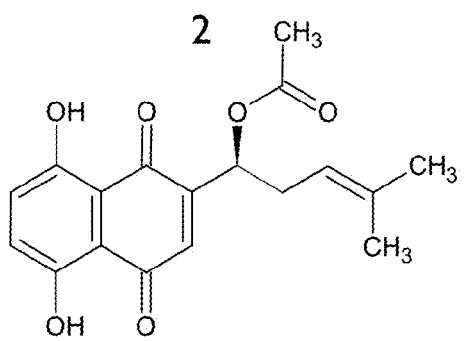
Figure 10:
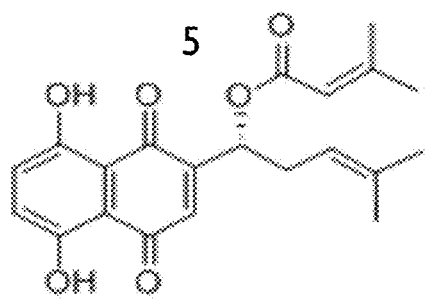
Figure 10:
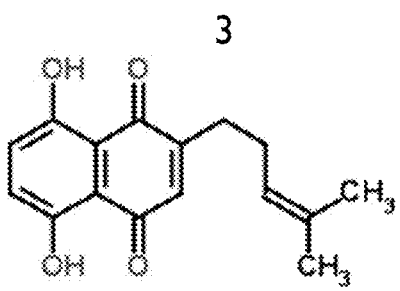
Figure 10:
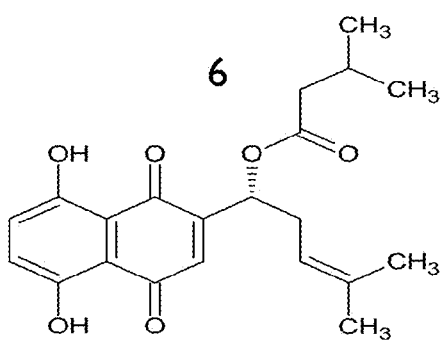

*Lithospermum erythrorhizon*, the purple gromwell, red-root gromwell, is a plant species in the genus *Lithospermum*. The dried root of *Lithospermum erythrorhizon* (lithospermum root or Lithospermi Radix, also referred to herein as "gromwell root") is known as a Chinese herbal medicine with various antiviral and biological activities, including inhibition of human immunodeficiency virus type 1 (HIV-1). It contains shikonin, deoxyshikonin, 1-eicosanol, isovalerylshikonin, 1-tetracosanol, caffeic acid, isobutyrylshikonin, 1-docosanol, stearyl alcohol, α-methyl-n-butyrylshikonin, β,β-dimethylacrylshikonin, lithospermidin A, lithospermidin B, β-hydroxyisobutyrylshikonin. FIG. 10 depicts molecular structures of some shikonin naphthoquinones phytochemicals present in a gromwell root extract.

As illustrated in FIG. 1A, gromwell root extract exhibits some unique transformative properties; pH titration triggers color change/polymerization. For example, this natural colorant transforms from red at a low pH to deep violet/purple above pH 8.0. pH triggered polymerization of gromwell root extract 0.10% (0.50% FLAVEX in adipate) in water-si chassis was activated by combination with acid gel. This is an example of a water-in-silicone composition combined with an acidic product, in which the color of the gromwell root extract transforms from purple to pink as a result of "triggering" with an acid.

However, to formulate gromwell root extract into a topical composition several technical disadvantages associated with the use of gromwell root extract in topical applications had to be overcome.

Figure 13:
FIG. 13 displays a picture of various concentrations of gromwell root extract imparting different shades of a "contouring" cheek gel application.

Gromwell root extract may stain clothing when it reacts with caustic treatments at concentrations of greater/=0.10% (FIG. 13). Another disadvantage relates to hydrolysis reactivity upon water exposure, leading to malodor (valerian acids) which can be minimized through anhydrous formulation, and/or harboring of the shikonin naphthoquinones to the external phase via water-in-oil or water-in-silicone emulsification. Additionally, the functional shikonin naphthoquinones exhibits very low solubility in conventional polar esters and lipophilic compounds used frequently in the topical industry. As such, without proper solubilization, resolidification, precipitation and polymerization of adduct compounds occurs preventing necessary penetration into skin/or hair for physiological function. Lastly, traditional natural oils leveraged in the skin health industry such as soybean, safflower and olive oil exhibit demonstrated solubility but prevent formulating as "oil-free" for consumers typically seeking oil-control products.

The gromwell extract and/or active compound may be extracted into an oil-free system by use of a $CO_2$ extraction method and secondary extraction with diisobutyl adipate via countercurrent liquid-liquid technique. This is described in detail in Example 1 below.

In one example, hexane extraction may also be used to obtain the gromwell extract. This technique uses hexane, as the solvent. Another example of an extraction technique that may be used to obtain an extract and/or active compound useful in the present invention is ethanol extraction, using ethanol as the solvent. Those of skill in the art will appreciate that temperature and pressure conditions can be varied to obtain the best yield of extract. This technique generates an extract of fat soluble and/or lipophilic compounds, similar to the total hexane extraction technique. Those of skill in the art will appreciate that there may be alternative extraction and purification processes, both known in the art and described in various patents and publications that can be used to obtain the extracts and/or active compound to be used in practicing the present invention.

The extract can then be standardized to 19-21% naphthoquinone, consisting of shikonin, acetylshikonin, deoxyshikonin, isobutyrylshikonin, isovalerylshikonin, α-methylbutyrylshikonin β-hydroxyisovalerylshikonin and β,β-dimethylacrylshikonin.

In one embodiment, the topical composition includes gromwell root extract in the amount sufficient to provide benefits to skin relating to sebum secretion and glycation in skin. Specifically, the extract or active of gromwell root (2% $CO_2$ custom extraction product in 88% diisobutyl adipate and 10% tocopherol), is present in an amount ranging from about 0.05% to about 10.0% by weight of the total composition; desirably, from about 0.05% to about 7.5% by weight of the total composition; more desirably, from about 0.05% to about 6% by weight of the total composition; more desirably, from about 0.05% to about 5.5% by weight of the total composition. In certain embodiments, the extract or active of gromwell root (2% $CO_2$ custom extraction product in 88% diisobutyl adipate and 10% tocopherol), is present in an amount of at least about 0.1% by weight of the total composition; at least about 0.5% by weight of the total composition; at least about 1.0% by weight of the total composition; at least about 2.0% by weight of the total composition; at least about 3.0% by weight of the total composition; at least about 5.0% by weight of the total composition; at least about 6.0% by weight of the total composition; at least about 7.0% by weight of the total composition; at least about 8.0% by weight of the total composition; at least about 9.0% by weight of the total composition; and up to about 10.0% by weight of the total composition.

As noted above, in order to achieve adequate penetration through the skin's formidable barrier, proper solubilization and formula vehicle design are necessary to achieve short and long term biological health benefits. To achieve this, and to ensure proper solubilization, free radical stabilization, strategic microphase placement, and combination with conducive microstructures for topical penetration, the described compositions also include a lipophilic solubilizer and a free radical stabilizer.

Examples of highly lipophilic solubilizers include non-comedogenic esters, such as adipates (e.g. diisobutyl adipate), caprylates, isononanoates (e.g., isononyl neopentanoate), and select ethoxylated triglycerides. Other solubilizers may include cetyl esters and PEG cetyl esters, hydrogenated polyisobutene, argan oil, soybean oil, and chemical UV filters/boosters such as Octisalate, Octinoxate, butyl octyl salicylate. In certain embodiments, the lipophilic solubilizers are present in an amount from about 1.0% to about 20.0% by weight of the composition.

Examples of free radical stabilizers include but are not limited to lipophilic antioxidants, such as tocotrienolss, carotenoids (e.g., tocopherol, tocopherol acetate, retinyl palmitate, tetrahexydecyl ascorbate, lutein, natural oils rich in unsaturated fatty acids such as docosahexaenoic acid and the like). Tocopherols are known to be strong antioxidants that trap peroxyl radicals in vivo, and carotenoids are the precursors of vitamin A. The free radical stabilizers aid in prevention of isomeric enantiomer phenomenon. In certain embodiments, the free radical stabilizers are present in an amount from about 0.10% to about 10.0% by weight of the composition.

The usage of low molecular weight non-comedogenic esters in combination with lipophilic antioxidant can properly protect and deliver gromwell while offering an "oil-free" formulation, advantageous to consumers with acne-prone, sensitive and oily skin.

Surprisingly, compositions containing a lipophilic antioxidant(s) and proper solubilizers prevent the enantiomer transition/color change phenomenon that occurs upon heating or light exposure providing consistent quality and optimal skin penetration to consumers.

The described formulations are also advantageously designed to inhibit polymerization of the underlying naphthoquinone compounds.

The delivery is further stabilized by combination with higher volume fraction of lipophilic continuous phases for topical microstructures, which simultaneously reduces the propensity for migration.

These compositions are further strategically designed to provide enhanced UV absorbance and/or boosting properties in the higher wavelength region to subsequently increase the protective anti-aging effect for consumers in established OTC sunscreen microstructures.

Exemplary identities of various constituents of the described emulsions and compositions are described below.

I. Vehicles

Suitable topical vehicles and vehicle components for use with the described formulations are well known in the cosmetic and pharmaceutical arts, and include such vehicles (or vehicle components) as water (e.g., purified and deionized); organic solvents such as alcohols (particularly lower alcohols readily capable of evaporating from the skin such as ethanol), glycols (such as propylene glycol, pentylene glycol, butylene glycol, and glycerol (glycerin)), aliphatic alcohols (such as lanolin); mixtures of water and organic solvents (such as water and alcohol), and mixtures of organic solvents such as alcohol and glycerol (optionally also with water); lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile) such as cyclomethicone, dimethiconol and dimethicone copolyol; hydrocarbon-based materials such as petrolatum, hydrogenated polyisobutene and squalane; emollient esters (such as diisobutyl adipate and caprylates), thickening agents (acrylates (carbomers), acrylamides, acryl taurates, hydroxyethylcellulose, methyl cellulose, xanthan gum, etc.) and other vehicles and vehicle components that are suitable for administration to the skin, as well as mixtures of topical vehicle components as identified above or otherwise known to the art. In certain embodiments, the topical vehicles and vehicle components are present in an amount from about 5% to about 70% by weight of the composition.

Figure 2:
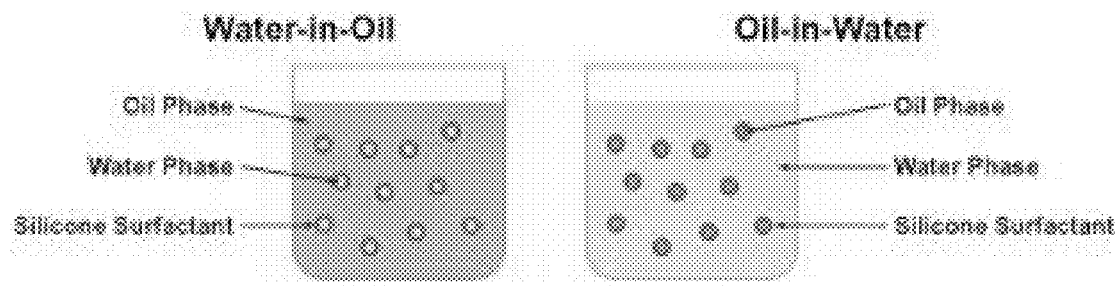
FIG. 2 depicts a schematic drawing of a water-in-silicone or silicone-in-water emulsion microstructure.

In one embodiment, the described compositions are water-in-silicone emulsions (see FIG. 2).

Figure 6:
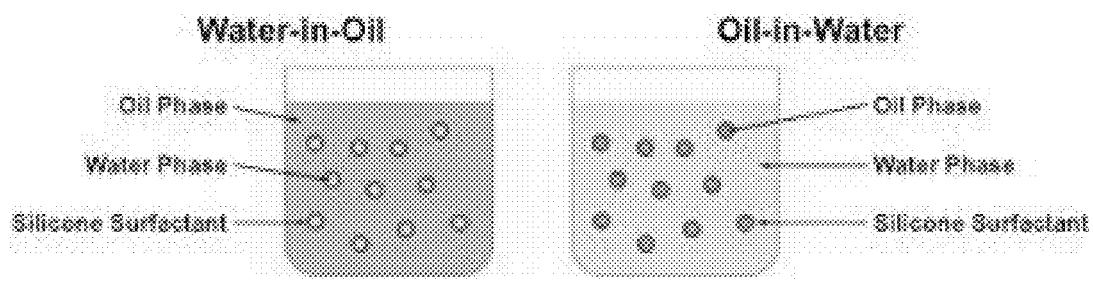
FIG. 6 depicts a schematic drawing of an oil-in-water and water-in-oil emulsion microstructure.

In another embodiment, the described compositions are oil-in-water emulsions (see FIG. 6). Liquids suitable for use in formulating the described compositions include water, and water-miscible solvents such as glycols (e.g., ethylene glycol, butylene glycol, isoprene glycol, propylene glycol, pentylene glycol), glycerol, liquid polyols, dimethyl sulfoxide, and isopropyl alcohol. One or more aqueous vehicles may be present. In certain embodiments, the liquids are present in an amount from about 10% to about 90% by weight of the composition.

2. Microstructures

Examples of microstructures include: lamellar lotion emulsification, anionic emulsification, anhydrous systems for lipcare/instant coverage via coloration, dual chamber liquid system with controlled isomeric/color-change, and water-in-oil emulsification for high volume fraction of lipophilic substances. In certain embodiments, the microstructures are present in an amount from about 5% to about 70% by weight of the composition.

3. Surfactants and Emulsifiers

Many topical formulations contain chemical emulsions, which use surface active ingredients (emulsifiers) to disperse dissimilar chemicals in a particular solvent system. For example, most lipid-like (oily or fatty) or lipophilic ingredients do not uniformly disperse in aqueous solvents unless they are first combined with emulsifiers, which form microscopic aqueous soluble structures that contain a lipophilic interior and a hydrophilic exterior, resulting in an oil-in-water emulsion. In order to be soluble in aqueous media, a molecule must be polar or charged so as to favorably interact with water molecules, which are also polar. Similarly, to dissolve an aqueous-soluble polar or charged ingredient in a largely lipid or oil-based solvent, an emulsifier is typically used which forms stable structures that contain the hydrophilic components in the interior of the structure while the exterior is lipophilic so that it can dissolve in the lipophilic solvent to form a water-in-oil emulsion. It is well known that such emulsions can be destabilized by the addition of salts or other charged ingredients which can interact with the polar or charged portions of the emulsifier within an emulsion droplet. Emulsion destabilization results in the aqueous and lipophilic ingredients separating into two layers, potentially destroying the commercial value of a topical product.

Surfactants suitable for use in the present invention may be ionic or non-ionic. These include, e.g., polysorbates (e.g., Polysorbate 20 (polyoxyethylene (20) sorbitan monolaurate), Polysorbate 40 (polyoxyethylene (20) sorbitan monopalmitate), Polysorbate 60 (polyoxyethylene (20) sorbitan monostearate), Polysorbate 80 (polyoxyethylene (20) sorbitan monooleate)), vegetable sorbitan stearates, steareth-10 (or other octadecyl polyoxyethylene ethers), sodium dodecyl sulfate (sodium lauryl sulfate), lauryl dimethyl amine oxide, cetyltrimethylammonium bromide (CTAB), polyethoxylated alcohols, polyoxyethylene sorbitan, octoxynol, N,N-dimethyldodecylamine-N-oxide, hexadecyltrimethylammonium bromide (HTAB), polyoxyl 10 lauryl ether, bile salts (such as sodium deoxycholate or sodium cholate), polyoxyl castor oil, nonylphenol ethoxylate, cyclodextrins, lecithin, dimethicone copolyol, lauramide diethanolamine (lauramide DEA), cocamide DEA, cocamide monoethanolamine (cocamide MEA), oleyl betaine, cocamidopropyl betaine, cocamidopropyl phosphatidyl PG-dimonium chloride, dicetyl phosphate (dihexadecyl phosphate), ceteareth-10 phosphate, polyglyceryl-2 triisostearate, cetyl PEG/PPG-1/1 dimethicone (ethoxylated or organo-modified silicones for W-in-Si emulsions, glyceryl stearate, glyceryl dilaurate, lecithin, unsaturated lecithin, etc.), and methylbenzethonium chloride. Appropriate combinations or mixtures of such surfactants may also be used according to the present invention.

Many of these surfactants may also serve as emulsifiers in the described formulations.

Other suitable emulsifiers include, but are not limited to, behentrimonium methosulfate-cetearyl alcohol, non-ionic emulsifiers like emulsifying wax, polyoxyethylene oleyl ether, polyethylene glycol-40 stearate (PEG-40 stearate), cetostearyl alcohol (cetearyl alcohol), ceteareth-12, ceteareth-20, ceteareth-30, ceteareth alcohol, glyceryl stearate, PEG-100 stearate, glyceryl stearate and PEG-100 stearate, steareth-2 and steareth-20, or combinations/mixtures thereof, as well as cationic emulsifiers like stearamidopropyl dimethylamine and behentrimonium methosulfate, or combinations/mixtures thereof.

In certain embodiments, the emulsifier or surfactant is present in an amount from about 0.5% to about 5% by weight of the composition. In certain embodiments, the emulsifier or surfactant is present in an amount from about 0.6% to about 4% by weight of the composition. In certain embodiments, the emulsifier or surfactant is present in about 0.6%, about 0.8%, about 1.0%, about 1.2%, about 1.4%, about 1.6%, about 2.05, about 2.5%, about 3.0%, about 3.5%, or about 4.0% by weight of the composition.

4. Moisturizers, Emollients, and Humectants

One important aspect of topical products in general, and cosmetic products in particular, is the consumer's perception of the aesthetic qualities of a product. Consumers highly value products that are aesthetically elegant and have an acceptable tactile feel and performance on their skin.

Suitable moisturizers for use in the formulations of the present invention include, but are not limited to, lactic acid and other hydroxy acids and their salts, glycerol, propylene glycol, pentylene glycol, butylene glycol, sodium salt of pyrrolidone carbonic acid (sodium PCA), sodium hyaluronate, or polyethylene glycol (PEG) (e.g., CARBOWAX PEG 200, CARBOWAX PEG 400, or CARBOWAX PEG 800).

Suitable emollients or humectants for use in the described formulations include, but are not limited to, cetyl palmitate, glycerol (glycerin), polypropylene glycol-15 stearyl ether (PPG-15 stearyl ether), lanolin alcohol, lanolin, lanolin derivatives, cholesterol, petrolatum, isostearyl neopentanoate, octyl stearate, mineral oil, isocetyl stearate, myristyl myristate, octyl dodecanol, 2-ethylhexyl palmitate (octyl palmitate), dimethicone, phenyl trimethicone, cyclomethicone, $C_{12}$-$C_{15}$ alkyl benzoates, dimethiconol, propylene glycol, pentylene glycol, *Theobroma grandiflorum* seed butter, shea butter, ceramides (e.g., ceramide 2 or ceramide 3), hydroxypropyl bispalmitamide MEA, hydroxypropyl bislauramide MEA, hydroxypropyl bisisostearamide MEA, 1,3-bis-(N-2-(hydroxyethyl)stearoylamino)-2-hydroxy propane, bis-hydroxyethyl tocopherylsuccinoylamido hydroxypropane, urea, aloe, allantoin, glycyrrhetinic acid, and dicaprylate/dicaprate.

In addition, appropriate combinations and mixtures of any of these moisturizing agents and emollients may be used.

In certain embodiments, a moisturizer, emollient, and/or humectant may be present in an amount from about 2% to about 30% by weight of the composition. In certain embodiments, the moisturizer, emollient, and/or humectant may be present in an amount from about 3% to about 12% by weight of the composition. In certain embodiments, the moisturizer, emollient, and/or humectant may be present in an amount of about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 10.5%, about 11%, about 11.5%, or about 12% by weight of the composition.

5. Preservatives and Antioxidants

The composition may further include components adapted to improve the stability or effectiveness of the applied formulation.

Suitable preservatives for use in the present invention include, e.g., ureas, such as imidazolidinyl urea and diazolidinyl urea; phenoxyethanol; sodium methyl paraben, methylparaben, ethylparaben, and propylparaben; potassium sorbate; sodium benzoate; sorbic acid; benzoic acid; formaldehyde; citric acid; sodium citrate; chlorine dioxide; quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; piroctone olamine; *Vitis vinifera* seed oil; and alcoholic agents, for example, chlorobutanol, dichlorobenzyl alcohol, phenylethyl alcohol, and benzyl alcohol.

Suitable antioxidants include, but are not limited to, ascorbic acid and its esters, sodium bisulfite, butylated hydroxytoluene, butylated hydroxyanisole, tocopherols (such as α-tocopherol), tocopheryl acetate, sodium ascorbate/ascorbic acid, ascorbyl palmitate, ascorbyl glucoside, propyl gallate, and chelating agents like ethylenediaminetetraacetic acid (EDTA) (e.g., disodium EDTA), citric acid, and sodium citrate.

In certain embodiments, antioxidants or preservatives of the present invention may also function as a moisturizer or emollient, or stabilizer for gromwell root, for example.

In addition, combinations or mixtures of these preservatives or anti-oxidants may also be used in the described formulations.

In certain embodiments, the antioxidant or preservative may be present in an amount from about 0.3% to about 0.9% by weight of the composition. In certain embodiments, the antioxidant or preservative may be present in an amount from about 0.4% to about 0.8% by weight of the composition. In certain embodiments, the antioxidant or preservative may be present in an amount of about 0.4%, about 0.5%, about 0.6%, about 0.7%, or about 0.8% by weight of the composition. Preservative enhancers which lower water activity such as propanediol, and pentylene glycol may also be used at concentrations from 1.0% to 7.0%.

6. Viscosity Modifiers

Suitable viscosity adjusting agents (i.e., thickening and thinning agents) include, but are not limited to, protective colloids or non-ionic gums such as hydroxyethylcellulose, xanthan gum, and *sclerotium* gum, as well as magnesium aluminum silicate, silica, microcrystalline wax, beeswax, paraffin, and cetyl palmitate. In addition, appropriate combinations or mixtures of these viscosity adjusters may be utilized.

7. Additional Constituents

In certain embodiments, additional constituents suitable for incorporation into the described compositions may include, but are not limited to: skin protectants, adsorbents, demulcents, emollients, moisturizers, buffering agents, sustained release materials, solubilizing agents, skin-penetration agents, skin soothing agents, deodorant agents, antiperspirants, sun screening agents, sunless tanning agents, vitamins, hair conditioning agents, anti-irritants, anti-aging agents, abrasives, absorbents, anti-caking agents, anti-static agents, astringents (e.g., witch hazel, alcohol, and herbal extracts such as chamomile extract), binders/excipients, buffering agents, chelating agents, film forming agents, conditioning agents, opacifying agents, lipids, pH adjusters (e.g., citric acid, sodium hydroxide, sodium phosphate monobasic, and sodium phosphate dibasic), or mixtures thereof.

For example, lipids normally found in healthy skin (or their functional equivalents) may be incorporated into the emulsions of the present invention. In certain embodiments, the lipid is selected from the group consisting of ceramides, cholesterol, and free fatty acids. In certain embodiments, the lipid is a ceramide. In certain embodiments, the lipid is selected from the group consisting of ceramide 1, ceramide 2, ceramide 3, ceramide 4, ceramide 5, ceramide 6, and mixtures thereof. In certain embodiments, the lipid is selected from the group consisting of hydroxypropyl bispalmitamide MEA, hydroxypropyl bislauramide MEA, hydroxypropyl bisisostearamide MEA, 1,3-bis-(N-2-(hydroxyethyl) stearoylamino)-2-hydroxy propane, and bis-hydroxyethyl tocopherylsuccinoylamido hydroxypropane.

Generally, the topical application is applied on at least a daily basis, preferably at least twice daily, and may be applied for any suitable period of time and/or as needed. Within hours, a user may notice improvement in suppressing sebum production in skin (e.g., seborrheic skin) and minimizing glycation in skin (e.g., mature skin), as well as other cosmetic improvements, such as reduction in imperfections of skin, reduction in shine, acne blemishes and improved adhesion of make-up, etc.

Examples of skin soothing agents include, e.g., allantoin, aloe, avocado oil, green tea extract, hops extract, chamomile extract, colloidal oatmeal, calamine, cucumber extract, dipotassium glycyrrhizate, licorice, willow bark, salicylates, gingerand combinations thereof. In certain embodiments, the skin smoothing agents are present in an amount from about 0.05% to about 5.0% by weight of the composition.

Examples of oils for hair care include, but are not limited to safflower oil, sunflower oil, chia oil, jojoba, meadowfoam seed oil, *perilla* oil, macadamia nut oil, almond oil, soybean oil, flaxseed oil, walnut oil. In certain embodiments, the oils are present in an amount from about 0.10% to about 10.0% by weight of the composition.

Examples of vitamins include, but are not limited to, vitamins A, D, E, K, and combinations thereof. In certain embodiments, the vitamins are present in an amount from about 0.10% to about 5.0% by weight of the composition.

Examples of sunscreens include, but are not limited to, p-aminobenzoic acid, avobenzone, cinoxate, dioxybenzone, homosalate, menthyl anthranilate, octocrylene, octyl methoxycinnamate, octyl salicylate, oxybenzone, padimate 0, phenylbenzimidazole sulfonic acid, sulisobenzone, titanium dioxide, trolamine salicylate, zinc oxide, 4-methylbenzylidene camphor, methylene bis-benzotriazolyl tetramethylbutylphenol, bis-ethylhexyloxyphenol methoxyphenyl triazine, terephthalylidene dicamphor sulfonic acid, drometrizole trisiloxane, disodium phenyl dibenzimidazole tetrasulfonate, diethylamino hydroxybenzoyl hexyl benzoate, octyl triazone, diethylhexyl butamido triazone, polysilicone-15, and combinations thereof. In certain embodiments, the sunscreen is present in an amount from about 0.5% to about 25% by weight of the composition.

Suitable fragrances and colors may be used in the formulations of the present invention. Examples of fragrances and colors suitable for use in topical products are known in the art. Examples of fragrances include, but are not limited to, bisabolol, *Melaleuca alternifolia* oil, *Melaleuca ericafolia* oil, and *Leptospermum petersonni* oil.

In certain embodiments, the fragrance or masking agents are present in an amount from about 0.05% to about 3.0% by weight of the composition. In certain embodiments, the fragrance is present in an amount from about 0.1% to about 1.6% by weight of the composition. In certain embodiments, the fragrance is present in an amount of about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, or about 1.6% by weight of the composition. Masking agents or odor masking constituents which can be directly declared on INCI label declarations for "fragrance-free" claims can also be incorporated. Suitable masking agents include but are not limited to (benzyl alcohol, pentadecalactones, jasmonates such as methydihydrojasmonate, aldehydes C14 (gamma undecalactone), ethylene brassylate, triethyl citrate, dihydro myrcenol (2,6-dimethyl-7-octen-2-ol) and hexyl acetates, geranyl acetate, linalyl acetate, ethyl linalool, helional (methylenedioxyphenyl methylpropanol), and eucaplyptol.

Other plant extracts, such as Aloe Vera, cornflower, witch hazel, elderflower, cucumber; as well as acerola cherry fermentate may also be included in the described formulations, but are optional.

Also, thickeners, activity enhancers, other colorants, and perfumes may be included in some embodiments. Cosmetic adjuncts can form the balance of the composition.

Additional skin benefit agents such as ceramides, glycoceramides, pseudoceramides, sphingolipids such as sphingomyelins, cerebrosides, sulphatides, and ganglioside, sphingosines, dihydrosphingosine, phytosphingosines, phospholipids, may also be incorporated, either separately or in mixtures.

In certain embodiments, the invention relates to a composition, which is a water-in-silicone emulsion, comprising:
- an extract or active of gromwell root (2% $CO_2$ custom extraction product in 88% diisobutyl adipate and 10% tocopherol), from about 0.5% to about 2% by weight of the composition;
- and, optionally, at least one of the following:
- Deionized water, from about 25% to about 75% by weight of the composition;
- Cyclopentasiloxane, from about 10% to about 20% by weight of the composition;
- Cetyl PEG/PPG-10/1 Dimethicone, from about 3% to about 5% by weight of the composition;
- Cyclopentasiloxane and Dimethicone/vinyl dimethicone crosspolymer, from about 2% to about 7% by weight of the composition;
- Hydrogenated Polyisobutene, from about 2% to about 4% by weight of the composition;
- Silica, from about 1% to about 5% by weight of the composition;
- Sensient Covabead, Polymethylmethacrylate (PMMA), 2MUSI, from about 3% to about 5% by weight of the composition;
- Glycerin, from about 1% to about 5% by weight of the composition;
- Xanthan gum, from about 0.05% to about 1% by weight of the composition;
- Sodium chloride, from about 0.1% to about 1% by weight of the composition;
- Pentylene Glycol [Hydrolite 5], from about 1% to about 5% by weight of the composition; or
- SymSave H [Hydroxyacetophenone], from about 0.1% to about 1% by weight of the composition.

In certain further embodiments, the invention relates to a composition, which is a water-in-silicone emulsion, comprising:
- an extract or active of gromwell root (2% $CO_2$ custom extraction product in 88% diisobutyl adipate and 10% tocopherol), from about 2.5% to about 7.5% by weight of the composition;
- and, optionally, at least one of the following:
- Deionized water, from about 25% to about 75% by weight of the composition;
- Cetyl PEG/PPG-10/1 Dimethicone, from about 4% to about 5% by weight of the composition;
- Cyclopentasiloxane, from about 10% to about 25% by weight of the composition;
- Cyclopentasiloxane and Dimethicone/vinyl dimethicone crosspolymer and dimethiconol, from about 2% to about 7% by weight of the composition;
- Glycerin, from about 1% to about 5% by weight of the composition;
- Xanthan gum, from about 0.05% to about 1% by weight of the composition;
- Sodium chloride, from about 0.1% to about 1% by weight of the composition;
- Pentylene Glycol [Hydrolite 5], from about 1% to about 5% by weight of the composition;
- Disteardimonium Hectorite, from about 0.1% to about 1% by weight of the composition;
- Titanium Dioxide encapsulated in Polymethylmethacrylate, from about 5% to about 10% by weight of the composition;
- PEG-60 Almond Trigylcerides, from about 0.5% to about 2.5% by weight of the composition;
- Disodium EDTA, from about 0.05% to about 1% by weight of the composition;
- Phenoxyethanol, from about 0.5% to about 1% by weight of the composition; or
- Neutrascent [Methyldihydrojasmonate (and) Tetramethyl Acetyloctahydronaphthalenes (and) Methylbenzyl Acetate (and) Hexyl Acetate (and) 3-Hexenol) and Dimethyl Heptenal] (Symrise), from about 0.1% to about 1% by weight of the composition.

In a further embodiment, the invention relates to a composition, which is an oil-in-water emulsion composition, comprising:
- an extract or active of gromwell root (2% $CO_2$ custom extraction product in 88% diisobutyl adipate and 10% tocopherol), from about 0.05% to about 1% by weight of the composition;
- and, optionally, at least one of the following:
- Water, purified, from about 25% to about 90% by weight of the composition;
- PEG-8, from about 1% to about 5% by weight of the composition;
- Aloe Vera Leaf Gel, from about 0.1% to about 2.5% by weight of the composition;
- Disodium EDTA, from about 0.05% to about 1% by weight of the composition;
- Allantoin, from about 0.05% to about 1% by weight of the composition;
- Glycerin, from about 1% to about 5% by weight of the composition;
- Xanthan gum, from about 0.05% to about 1% by weight of the composition;
- Hydroxyethylcellulose, from about 0.1% to about 2% by weight of the composition;
- Dipotassium Glycyrrhizate, from about 0.1% to about 1% by weight of the composition;
- Zinc PCA, from about 0.1% to about 1% by weight of the composition;
- SD Alcohol-40, from about 1% to about 10% by weight of the composition;
- Butylene Glycol, from about 0.5% to about 2% by weight of the composition;
- Propanediol, from about 0.5% to about 5% by weight of the composition;
- Pentylene Glycol, from about 0.5% to about 5% by weight of the composition;
- Salicylic Acid, from about 0.5% to about 2% by weight of the composition;
- Triethanolamine, from about 0.1% to about 1% by weight of the composition;
- Dimethicone and Water and Ceteth-10 and Laureth-4 [Dow Corning 7-3099 HIP Emulsion], from about 5% to about 10% by weight of the composition;
- PEG-60 Almond Glycerides, from about 0.1% to about 1% by weight of the composition;
- Tocopheryl Acetate, from about 0.1% to about 1% by weight of the composition;
- Polyacrylamide (and) C13-14 Isoparaffin (and) Laureth-7, from about 1 to about 5% by weight of the composition;
- Witch Hazel and Alcohol, from about 1% to about 5% by weight of the composition;
- Propylene Glycol and *Citrus Limon* (Lemon) and Cucumber Extract, from about 1% to about 5% by weight of the composition;
- Water and *Camellia Sinensis* Leaf Extract [Green Tea] and Butylene Glycol, from about 0.5% to about 2% by weight of the composition;
- Butylene Glycol (and) Water (and) *Spiraea* Ulmaria Extract, from about 1% to about 5% by weight of the composition; or Benzyl Alcohol, from about 0.1% to about 1% by weight of the composition.

In a further embodiment, the invention relates to a composition, which is an oil-in-water emulsion composition, comprising:

an extract or active of gromwell root (2% $CO_2$ custom extraction product in 88% diisobutyl adipate and 10% tocopherol), from about 0.1% to about 5% by weight of the composition;

and, optionally, at least one of the following:

Water, purified, from about 25% to about 90% by weight of the composition;

Allantoin, from about 0.05% to about 1% by weight of the composition;

Propanediol, from about 0.5% to about 5% by weight of the composition;

Pentylene Glycol, from about 0.5% to about 5% by weight of the composition;

Hydroxyacetophenone [SymSave H]—preservative booster Symrise, from about 0.1% to about 1% by weight of the composition;

Polyglycerol-2 Triisostearate, from about 2% to about 5% by weight of the composition;

Octyl Salicylate [Octisalate], from about 2.5% to about 10% by weight of the composition;

Red 7 lake Slurry [Kobo INBP45R7C], from about 0.1% to about 1% by weight of the composition;

Butyl Octyl Salicylate, from about 0.5% to about 5.0% by weight of the composition;

Synthetic Fluorphlogopite and Titanium Dioxide [Timiron Synwhite 40], from about 0.5% to about 2.5% by weight of the composition;

Sodium Polyacrylate, from about 0.5% to about 2.5% by weight of the composition;

Ethyl Vanillin and *Helianthus Annuus* (Sunflower) Seed Oil, from about 0.05% to about 1% by weight of the composition; or Grapefruit Oil, from about 0.05% to about 1% by weight of the composition.

Custom Masking Blend [Hedione-methyldihydrojasmonate, Dihydro myrcenol-2,6-dimethyl-7-octen-2-ol, Aldehyde C14-gamma-undecalactone] at 0.10% to 1.0% by weight of composition In yet a further embodiment, the invention relates to a composition, which is an oil-in-water emulsion composition, comprising:

an extract or active of gromwell root (2% $CO_2$ custom extraction product in 88% diisobutyl adipate and 10% tocopherol), from about 2.5% to about 7.5% by weight of the composition;

and, optionally, at least one of the following:

Water, purified, from about 25% to about 90% by weight of the composition;

Hydroxyethylcellulose, from about 0.5% to about 2% by weight of the composition;

Phosphoric Acid, from about 0.1% to about 1% by weight of the composition;

Stearamidopropyl Dimethylamine, from about 0.5% to about 2.5% by weight of the composition;

Preservative premix (Butylene Glycol and Glycerin and Methylparaben and chlorphenesin, from about 2% to about 5% by weight of the composition;

Polysorbate 20, from about 0.1% to about 1% by weight of the composition;

Glyceryl Stearate, from about 2% to about 10% by weight of the composition;

Glyceryl Dilaurate—neutralized, from about 2% to about 10% by weight of the composition;

Hydrogenated Polyisobutene, from about 1% to about 5% by weight of the composition;

Diisobutyl adipate, from about 2% to about 10% by weight of the composition;

PEG-60 Almond Triglyceride, from about 1% to about 2.5% by weight of the composition;

Glycerin and Bisabolol and Ginger Extract, from about 0.5% to about 2.5% by weight of the composition; or Neutrascent [Methyldihydrojasmonate (and) Tetramethyl Acetyloctahydronaphthalenes (and) Methylbenzyl Acetate (and) Hexyl Acetate (and) 3-Hexenol) and Dimethyl Heptenal] (Symrise), from about 0.1% to about 0.5% by weight of the composition.

Custom Masking Blend [Symrise: Hedione-methyldihydrojasmonate, Dihydro myrcenol-2,6-dimethyl-7-octen-2-ol, Aldehyde C14-gamma-undecalactone] at 0.10% to 1.0% by weight of composition In yet a further embodiment, the invention relates to a composition, which is an oil-in-water emulsion composition, comprising:

an extract or active of gromwell root (2% $CO_2$ custom extraction product in 88% diisobutyl adipate and 10% tocopherol), from about 1.0% to about 5% by weight of the composition;

and, optionally, at least one of the following:

Water, purified, from about 25% to about 50% by weight of the composition;

Aloe Vera Leaf powder, from about 0.01% to about 0.5% by weight of the composition;

Glycerin, from about 1% to about 10% by weight of the composition;

Xantham Gum, from about 0.1% to about 1% by weight of the composition;

Montmorillonite, from about 5% to about 10% by weight of the composition;

Dipotassium Glycyrrhizinate, from about 0.05% to about 1% by weight of the composition;

Disodium EDTA, from about 0.05% to about 0.5% by weight of the composition;

Allantoin, from about 0.05% to about 0.5% by weight of the composition;

Panthenol, from about 0.05% to about 0.5% by weight of the composition;

Unsaturated Lecithin [+Phospholipid], from about 0.5% to about 2.0% by weight of the composition;

Vegetable Sorbitan Stearate, from about 0.5% to about 2.0% by weight of the composition;

BIS-PEG-18 Methyl Ether Dimethyl Silane, from about 1% to about 5% by weight of the composition;

Tocopheryl Acetate, from about 0.1% to about 1% by weight of the composition;

Emulsifying WaxNF, from about 0.5% to about 5% by weight of the composition;

Behenyl Alcohol, from about 0.5% to about 5% by weight of the composition;

Polysorbate 20, from about 1.0% to about 5% by weight of the composition;

Hydrogenated Polyisobutene, from about 1.0% to about 5% by weight of the composition;

C12-C15Alkyl Benzoate, from about 1% to about 10% by weight of the composition;

Cetyl Dimethicone, from about 0.5% to about 5% by weight of the composition;

Glyceryl Dilaurate—neutralized, from about 0.5% to about 5% by weight of the composition;

PEG-60 Almond Glycerides, from about 0.5% to about 2.0% by weight of the composition;

Precipitated Sulfur, from about 1% to about 10% by weight of the composition;

Green Tea Extract (and) Butylene Glycol, from about 0.5% to about 2.0% by weight of the composition;

Glutathione, from about 0.05% to about 2.0% by weight of the composition;

Witch Hazel and Alcohol, from about 1% to about 5.0% by weight of the composition;

Water and Butylene Glycol and Cucumber (*Cucumis Sativus*) Fruit Extract and Sorbitol, from about 0.1% to about 2.5% by weight of the composition;

Butylene Glycol (and) Water (and) *Spiraea* Ulmaria Extract, from about 0.5% to about 5.0% by weight of the composition;

Liposomal Preparation with Licorice Embedment, from about 0.5% to about 2.5% by weight of the composition;

Glycerin and Water and Butylene Glycol and Ceramide 3 and Beta Sitosterol (Liposomal Preparation with Ceramide), from about 0.5% to about 5% by weight of the composition;

Benzyl Alcohol, from about 0.1% to about 2.0% by weight of the composition;

PEG-60 Almond Glycerides, from about 0.5% to about 2.5% by weight of the composition;

Neutrascent [Methyl dihydrojasmonate] (Symrise) (and) Tetramethyl Acetyloctahydronaphthalenes (and) Methylbenzyl Acetate (and) Hexyl Acetate (and) 3-Hexenol and Dimethyl Heptenal], from about 0.05% to about 1.0% by weight of the composition;

Pentylene Glycol [Hydrolite 5], from about 0.5% to about 3.0% by weight of the composition; or Chlorphenesin, from about 0.15% to about 0.29% by weight of the composition.

Custom Masking Blend [Symrise: Hedione-methyldihydrojasmonate, Dihydro myrcenol-2,6-dimethyl-7-octen-2-ol, Aldehyde C14-gamma-undecalactone] at 0.10% to 1.0% by weight of composition In certain embodiments, the pH of the composition may be from about 3.6 to about 8.0. In certain embodiments, the pH of the composition is from about 4.5 to about 7.5. In certain embodiments, the pH of the composition is about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0.

Uses

A particularly preferred embodiment relates to a cosmetic treatment system utilizing the described, topical composition suitably formulated for suppressing sebum production in skin (e.g., seborrheic skin) and/or minimizing glycation in skin (e.g., mature skin) to inhibit, prevent or reduce AGEs.

In certain embodiments, the described compositions, comprising gromwell root, tocopherol, and diisobutyl adipate, may be used as facial mattifiers or finishers. In this regard, optionally, such composition can include oil absorptive particles, such as silica and monodisperse poly(methyl methacrylate) (PMMA). These compositions are oil-free face finishers, mattifiers or primers that immediately upon application can reduce skin imperfections and shine, leverage hints of natural pink (gromwell root) to neutralize skin yellowness or sallowness. The compositions have a lightweight texture providing for optimum blending on all skin tones. The compositions can be used under, over, or custom blended with foundation for effect (there are 50 shades of pink for gromwell, which allow one to create a healthy complexion). Foundation blending concept involves personalization. Surprisingly, the composition combines oil absorption with control of sebum production and natural colorant benefit.

FIG. 2 illustrates a water-in-silicone emulsion microstructure. Exemplary compositions may be used as facial mattifiers (e.g., sebum absorptive and anti-productive), sunscreen with inorganic filters (e.g., blemish balms, pink protective primers), and color changing cheek stains.

In certain further embodiments, the described compositions, comprising gromwell root, tocopherol, and diisobutyl adipate, may be used as UV protective blemish compositions, such as a balm, lotion, or cream. The compositions may have any suitable SPF, e.g., 5, 7, 10, 15, 20, 30, 45, or 50. The composition may also include encapsulated iron oxides—pigments for color change from pink to flesh tone.

In certain embodiments, the described compositions, comprising gromwell root, tocopherol, and diisobutyl adipate, may be used as facial primers/illuminator compositions (e.g., pearlescent pink primers/illuminator). The composition instantly upon application, illuminates skin with a radiant glow, thus reducing skin imperfections and creates a radiant, rosy glow complexion, and leverages hints of natural pink (gromwell root) to neutralize skin yellowness or sallowness.

In certain embodiments, the described composition may be used under, over, or custom blended with foundation for effect.

Optionally, the described composition may include interlayered mica with titanium dioxide. The resultant formulation is a silicone high internal phase emulsion. A quasi-drug version may include ascorbyl glucoside. Such composition provides optimum blending and transparency on all skin tones/types without white cast, is lightweight with innovative texture and easily incorporates into any basic skincare regime.

The described compositions aid in management of dermatosis, such as seborrheic dermatitis, and/or minimizing glycation in skin (e.g., mature skin).

Exemplary oil-in-water compositions may be anti-blemish treatment gels (over the counter with an active for controlling sebum secretion and cushion cheek jelly), cationic conditioning treatments (facial firming or coloring retentive), and nighttime anti-blemish spot treatment compositions (e.g., over the counter suspension with sulfur).

In certain embodiments, the exemplary lamellar (oil-in-water emulsion) lotion and sulfur suspension (rich in anti-inflammatories, sebum suppressive ingredients, such as licorice, green tea, precipitated sulfur and mineral based clays) formulation may be suitable for holistic treatment of all causative factors of acne. The lamellar emulsification system drives increased skin surface adhesion and longer retention of moisturization through its similar chemical structure to the skin's intercellular lamellae lipids.

In certain embodiments, viscosity of emulsion through usage of different thickening systems, and lipophilic solubilizers for gromwell root extract may be varied. For example, viscosity test results range from approximately 6,000 centipoise to 100,000 centipoise for serums/gels to viscous cream applications respectively. However, without full solubilization and stabilization of naphthoquinones polymerization lipophilic antioxidants the consumer would experience a visibly inconsistent product reducing quality/biological performance, control and confidence in resale.

Figure 11:
FIG. 11 depicts a picture of containers with various extract "shades of pink" formulation prototypes.
Figure 12:
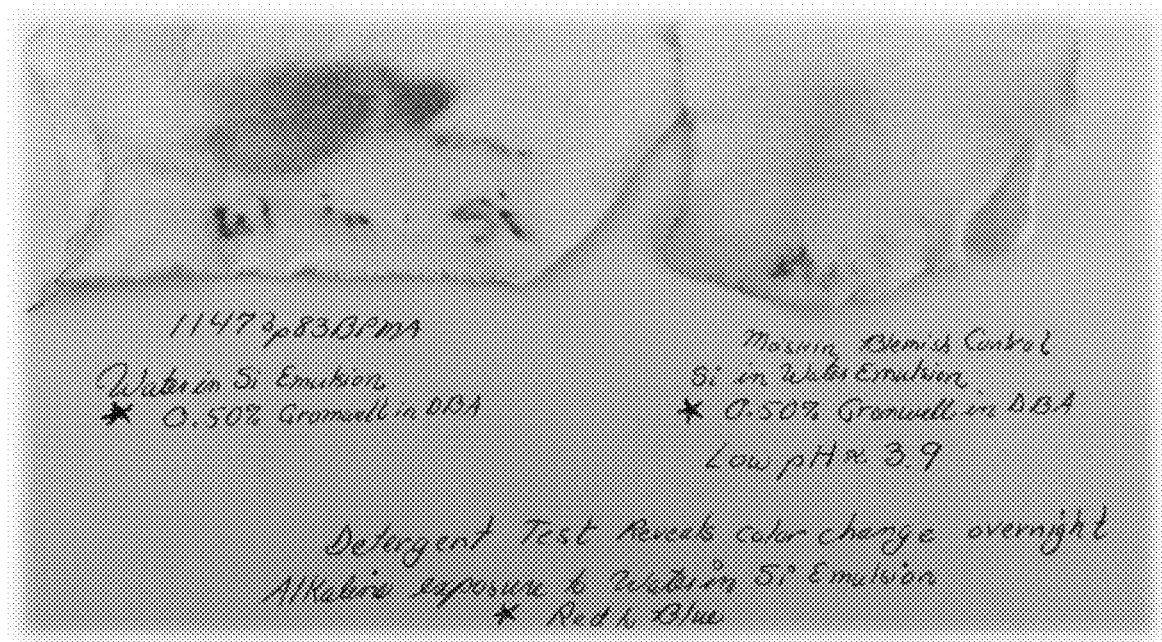
FIG. 12 depicts a picture that illustrates complexation of gromwell root in the presence of high caustic detergent levels, which induces staining of clothing.

FIG. 11 depicts a picture of containers with various gromwell root extract "shades of pink" formulation prototypes.

Methods

Certain embodiments relate to a method for treating oily skin associated with dermatosis in a subject in need thereof comprising applying to an affected area of the subject a therapeutically-effective amount of a composition comprising *Lithospermum erythrorhizon*, a lipophilic solubilizer, and a free radical stabilizer. The dermatosis may be seborrheic dermatitis, where the subject may present with desquamation, erythema, pruritus, inflammation, lichenification, excoriation, stinging, scaling, or increased sebum production. The affected area may be the scalp, including the hairline, ear canals, or behind the ears; the face, including the eyebrows, nose, or nasolabial folds; and the trunk, including the chest or back. The composition may be applied once daily or twice daily, or as needed.

Certain further embodiments relate to a method for minimizing glycation in mature skin in a subject in need of the treatment comprising applying to the subject a composition comprising a therapeutically effective amount of *Lithospermum erythrorhizon*, a lipophilic solubilizer, and a free radical stabilizer. The subject may present with wrinkling, loss of skin elasticity, skin stiffness, accelerated skin aging, compromised skin barrier function, loss of volume in the face due to redistribution of fat. The composition may be applied once daily or twice daily, or as needed.

Certain further embodiments relate to a method for inhibiting, reducing or preventing AGEs in the skin of a subject in need of the treatment comprising applying to the subject a composition comprising a therapeutically effective amount of *Lithospermum erythrorhizon*, a lipophilic solubilizer, and a free radical stabilizer.

The following are illustrative examples of formulations and compositions according to this invention. Although the examples use only selected compounds and formulations, it should be understood that the following examples are illustrative and not limited.

In the following Examples, provided are seven formulations exhibiting proper stabilization of gromwell root extract leveraging numerous microstructures: water in silicone emulsification for facial mattifier and sunscreen application, translucent gel for anti-blemish application, cheek color in cushion jelly format, lamellar oil-in water cream, and anhydrous gelled oil lip gloss for increased surface adhesion and skin firmness. Proper solubilization involves dissolving gromwell into various lipophilic agents at concentrations which achieve transparency and avoidance of precipitation upon shelf exposure/standing conditions. Experimentation has demonstrated the unique usage of highly non-polar esters (preferred diisobutyl adipate or caprylates) for proper solubilization of the shikonin naphthoquinones compounds in combination with lipophilic antioxidants to prevent undesired polymerization.

High performance chromatography characterization of prototype variants reveals prevention of formation of insoluble polymerized napthoquinones through controlled processing conditions and minimizing exposure to Lewis acids (such as ZnO, ZnCl, Iron Oxides) and basic compounds.

EXAMPLES

Example 1: Preparation of Gromwell Root Extract

Gromwell root was custom $CO_2$ extracted with a secondary countercurrent lipophilic extraction in diisobutyl adipate to a standardized concentration of shikonin naphthoquinones (shikonin, acetylshikonin, ß-hydroxyisovalerylshikonin, deoxyshikonin, Isobutyrylshikonin, β,β-dimethylacrylshikonin, isovalerylshikonin and alpha-methybutyrylshikonin) at about 19 to 21%. This 20% blend was further solubilized in 88% diisobutyl adipate with 10% tocopherol with standard mixing equipment at temperatures below T=120° F. to achieve 2% concentration of gromwell root.

Example 2: Oil-Free Facial Mattifier/Primer Formulation

Table 1 shows an exemplary oil-free facial mattifier formulation.

TABLE 1

Raw Material Description for Oil-Free Facial Mattifier Formulation

| | % |
|---|---|
| Gromwell root extract (2% $CO_2$ custom extraction product in 88% diisobutyl adipate and 10% tocopherol) | 1.0000 |
| Cyclopentasiloxane | 15.000 |
| Cetyl PEG/PPG-10/1 Dimethicone | 4.5000 |
| Cyclopentasiloxane and Dimethicone/vinyl dimethicone crosspolymer | 5.0000 |
| Hydrogenated Polyisobutene | 3.0000 |
| Silica | 2.0000 |
| Optical Diffuser, Monodisperse particles of polymethylmethacrylate from Sensient Covabead, Polymethylmethacrylate (PMMA), 2MUSI | 3.5000 |
| Deionized water | 58.900 |
| Glycerin | 3.0000 |
| Xanthan gum | 0.1000 |
| Sodium chloride | 0.5000 |
| Pentylene Glycol [Hydrolite 5] | 3.0000 |
| SymSave H [Hydroxyacetophenone] | 0.5000 |

A pink facial primer was shown to immediately reduce imperfections and shine featuring gromwell root extract to neutralize sallowness/yellowness and oil absorptive particles, such as silica and polymethylmethacrylate. The formulation's lightweight, innovative, water-in-silicone emulsion microstructure was shown to aid in even distribution of high particle concentrations; while properly stabilizing gromwell root extract for long-term biological activity.

Figure 3:
FIG. 3 is a photograph showing exemplary oil-free facial mattifier compositions' stability at 2.5 months at ambient conditions (A) and at 50° C. (B).
Figure 23:
FIG. 23 depicts a photograph of gromwell lip & cheek jelly prototypes at 6 months at 40° C. exposure (L) as compared to 6 months at 25° C. exposure (R).

FIG. 3 is a photograph showing exemplary Oil-Free Facial Mattifier compositions' stability at 2.5 months at ambient conditions and at 50° C. As shown in the photograph, the composition was stable at ambient conditions as well as at 50° C. following storage for 2.5 months. A similar composition was prepared as shown in the image of FIG. 23 (described in Example 14 below) with six months of favorable stability under elevated temperature.

Figure 4:
FIG. 4 depicts a photograph showing exemplary compositions undergoing controlled and uncontrolled isomerization followed by subsequent polymerization.

FIG. 4 depicts a photograph showing exemplary compositions undergoing controlled and uncontrolled polymerization of shikonin naphthoquinone. This image illustrates prototypes of water-in-silicone emulsions of similar base constituents with and without exposure to heat and UV. The leftmost vial reflects UV exposure to the emulsion in the absence of lipophilic antioxidants resulting in notable darkening of color. The center jars show the proper stabilization of color through solubilization of gromwell in the Adipate ester combined with tocopherol. The rightmost vial reflects a "smart cheek stain" concept which exaggerates the polymerization through high concentrations of porous silica and electrolytic phase which can triggered to transform from purple to pink through combination with an acidic gellant.

Figure 5:
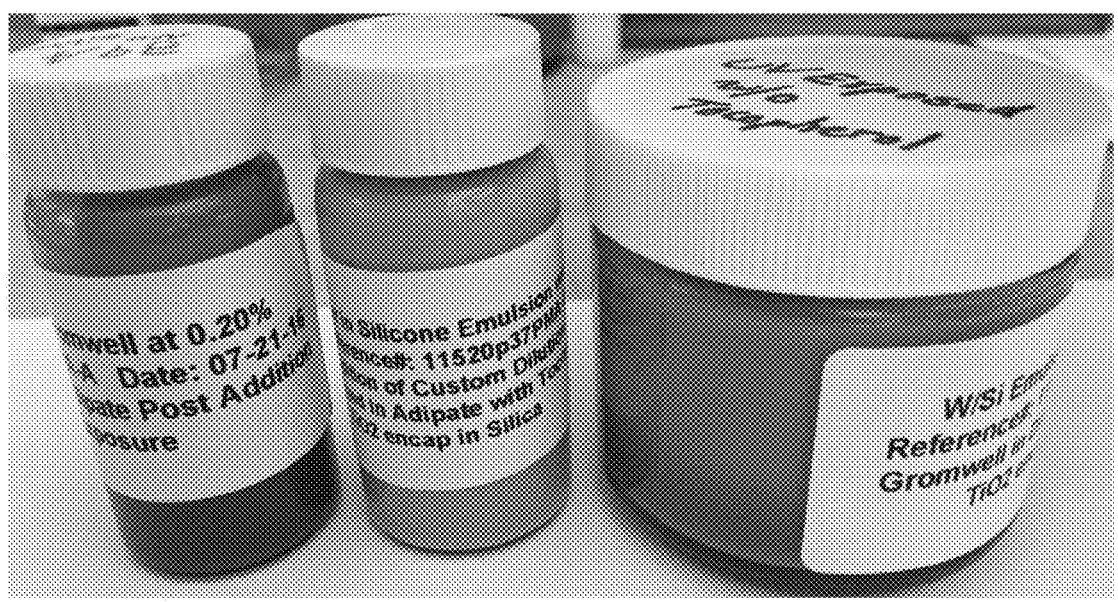
FIG. 5 depicts a photograph showing exemplary compositions undergoing controlled and uncontrolled isomerization followed by subsequent polymerization.

Referring to FIG. 5, improper stabilization of the polymerization, in which color transition occurs upon exaggerated exposure to UV, heat, and electrolytic catalysis is shown. This undesirable phenomenon is compared to similar base formulations stabilized with lipophilic anti-oxidant and solubilized adipate ester.

Example 3: UV Protective Anti-Blemish Balm with SPF20

Table 2 shows an exemplary UV protective blemish balm formulation.

TABLE 2

Raw Material Description for UV Protective Blemish Balm Formulation

| | % |
|---|---|
| Gromwell root extract (2% $CO_2$ custom extraction product in 88% diisobutyl adipate and 10% tocopherol) | 5.0000 |
| Cyclopentasiloxane | 22.000 |
| Cetyl PEG/PPG-10/1 Dimethicone | 3.5000 |
| Octinoxate | 7.5000 |
| Cyclopentasiloxane and Dimethicone/vinyl dimethicone crosspolymer and dimethiconol | 5.5000 |
| Disteardimonium Hectorite | 0.4000 |
| Titanium Dioxide encapsulated in Polymethylmethacrylate | 7.1500 |
| PEG-60 Almond Triglycerides | 1.5000 |
| Deionized Water | 42.600 |
| Glycerin | 3.0000 |
| Disodium EDTA | 0.2000 |
| Xanthan Gum | 0.1000 |
| Sodium chloride | 0.5000 |
| Phenoxyethanol | 0.8000 |
| Neutrascent | 0.2500 |

A oil-free facial sunscreen providing broad spectrum UV protection that immediately reduces imperfections using gromwell root extract to neutralize yellowness/sallowness and encapsulated UV physical filters for optimal blending on all skin tones.

Further isolated experimentation revealed the additive UV absorptive properties of the naphthoquinone underlying structure through evaluation under the standardized instrumental technique for prediction of Sun Protection Factor and Critical Wavelength for UVA protective performance.

Table 3 provides indication of a higher wavelength of absorbance for gromwell root similar to established UV A organic filtering agents.

TABLE 3

UV Absorption of Various Lipophilic Agents

| | GR Skincare % of Formula | GR/AVO % of Formula | AVO % of Formula | GR Lipcare % of Formula |
|---|---|---|---|---|
| *Lithospermum Erythrorhizon* (Gromwell Root) $CO_2$ extraction | 2.00 | 2.00 | | 2.00 |
| Avobenzone [UV A absorber] | | 3.00 | 3.00 | |
| Diisobutyl Adipate | 97.00 | 94.00 | 97.00 | |
| *Simmondsia Chinensis* (Jojoba) Oil and *Arganica Spinosa* Kernel Oil (Argan) and Tocopheryl Acetate and Bisabolol | | | | 97.00 |
| Tocopherol | 1.00 | 1.00 | | 1.00 |
| in vitro UV SPF Result (ISO 24443) | 1.30 | 4.99 | 2.98 | 1.14 |
| CRITICAL WAVELENGTH [nm] | 384.00 | 381.07 | 378.53 | 379.01 |

Example 4: Medicated Anti-Blemish Treatment Gel

Table 4 provides an exemplary medicated anti-blemish treatment formulation (in pink gel).

TABLE 4

Raw Material Description for Medicated Anti-Blemish Treatment Formulation

| | % |
|---|---|
| Gromwell root extract (2% $CO_2$ custom extraction product in 88% diisobutyl adipate and 10% tocopherol) | 0.1000 |
| Water, Purified | 65.300 |
| *Aloe Vera* Leaf Gel | 1.0000 |
| Disodium EDTA | 0.1000 |
| Allantoin | 0.2000 |
| Glycerin | 2.0000 |
| Hydroxyethylcellulose | 0.6000 |
| Xanthan Gum | 0.1500 |
| Dipotassium Glycyrrhizate | 0.2000 |
| Zinc PCA | 0.2500 |
| SD Alcohol-40 | 5.0000 |
| PEG-8 | 2.5000 |
| Butylene Glycol | 1.1000 |
| Propanediol | 1.0000 |
| Pentylene Glycol | 1.0000 |
| Salicylic Acid | 1.1000 |
| Triethanolamine | 0.6500 |
| Dimethicone and Water and Ceteth-10 and Laureth-4 [Dow Corning 7-3099 HIP Emulsion] | 7.5000 |
| PEG-60 Almond Glycerides | 0.2500 |
| Tocopheryl Acetate | 0.5000 |
| Polyacrylamide (and) C13-14 Isoparaffin (and) Laureth-7 | 2.0000 |
| Witch Hazel and Alcohol | 2.0000 |
| Propylene Glycol and *Citrus Limon* (Lemon) and Cucumber Extract | 2.0000 |
| Water and *Camellia Sinensis* Leaf Extract [Green Tea] and Butylene Glycol | 1.0000 |
| Butylene Glycol (and) Water (and) *Spiraea Ulmaria* Extract | 2.0000 |
| Benzyl Alcohol | 0.5000 |

Figure 7:
FIG. 7 depicts a picture of containers containing medicated anti-blemish treatment formulation, when stored at 50° C. for 3 months as compared to storage at ambient conditions for 3 months.

FIG. 7 depicts a picture illustrating the medicated anti-blemish treatment formulation (3-month stability study when kept at 50° C. and at ambient temperature). The formulation is stable as an anti-acne treatment with pH range of 3.6-4.2, viscosity of 9,000 to 20,000 cP., quantitative detection of salicylic acid at 0.99% to 1.21% and microbial self-sterilization in <2 days.

Figure 8:
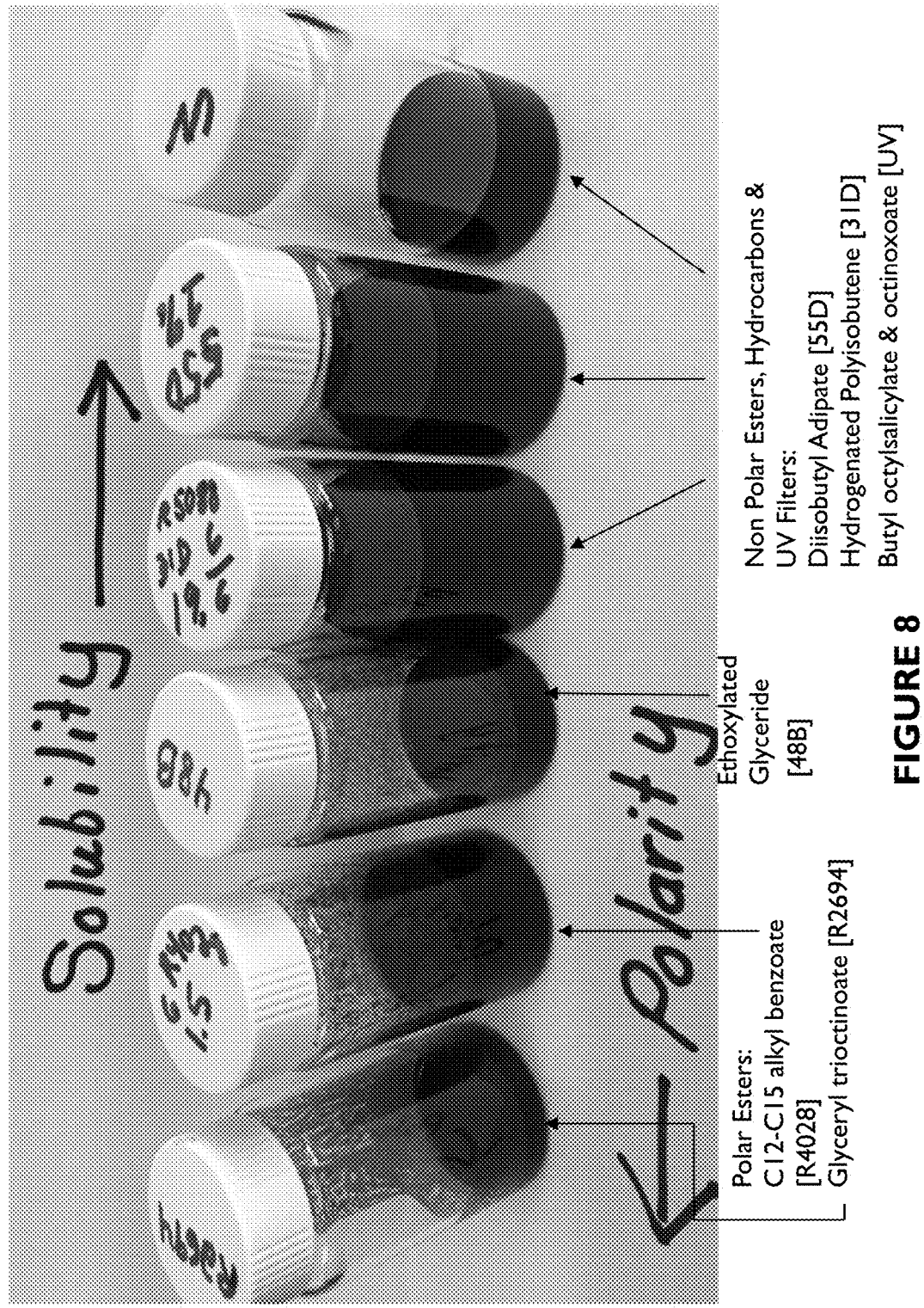
FIG. 8 depicts a picture of containers with various lipophilic agents for use with gromwell root extract comparing solubility versus polarity of the various agents.

FIG. 8 depicts results of the solubility vs. polarity study of various lipophilic agents for gromwell. Experimentation for solubility involves blending gromwell at initial dilutions of 10%, followed by 5%, 2.0% and 1.0% until homogeneity and transparency was achieved upon standing.

A translucent, oil-free pink hydro-alcoholic gel containing salicylic acid for the treatment of acne. Contains a multi-functional botanical blend to holistically address the primary factors of acne (gromwell root extract for oil control, licorice and aloe to sooth blemishes, and meadowsweet for balancing microflora/anti-microbial benefit).

Example 5: Contouring Cheek Jelly

Table 5 provides an exemplary contouring cushion crème jelly formulation for cheek and face application.

TABLE 5

Raw Material Description for Contouring Cushion Crème Jelly Formulation

| | % |
|---|---|
| Gromwell root extract (2% $CO_2$ custom extraction product in 88% diisobutyl adipate and 10% tocopherol) | 0.5000 |

TABLE 5-continued

Raw Material Description for Contouring Cushion Crème Jelly Formulation

| | % |
|---|---|
| Water Purified | 82.650 |
| Allantoin | 0.2000 |
| Propanediol (Zemea) | 2.0000 |
| Pentylene Glycol [Hydrolite 5] | 2.0000 |
| Hydroxyacetophenone [SymSave H] - preservative booster Symrise | 0.5000 |
| Polyglycerol-2 Triisostearate | 3.5000 |
| Octyl Salicylate [Octisalate] | 5.0000 |
| Red 7 lake Slurry [Kobo INBP45R7C] | 0.2500 |
| Butyl Octyl Salicylate | 1.0000 |
| Synthetic Fluorphlogopite and Titanium Dioxide [Timiron Synwhite 40] | 1.0000 |
| Sodium Polyacrylate | 1.2000 |
| Ethyl Vanillin and *Helianthus Annuus* (Sunflower) Seed Oil | 0.1000 |
| Grapefruit Oil | 0.1000 |

FIG. 13 captures variations of concentration of gromwell to achieve different shades of cheek jellies solubilized in diisobutyl adipate, tocopherol and butyl octyl salicylate.

A translucent, pink to rose gel providing an immediate rosy glow blushing benefit in a unique water-based, cooling formula. The concentration of gromwell and volume fraction of lipophilic emollients impacts the shade of contouring effect achieved upon application to the skin.

A similar formula (described in Example 13 below) is an adaptation of the concept to a lip and cheek application including 3 months of favorable stability at elevated temperatures.

Example 6: Cationic Conditioning Crème for Leave-on Hair or Facial-Treatment Applications Table 6 provides an exemplary cationic conditioning crème formulation for leave-on hair or facial-treatment applications.

TABLE 6

Raw Material Description for Cationic Conditioning Crème Formulation

| | % |
|---|---|
| Gromwell root extract (2% $CO_2$ custom extraction product in 88% diisobutyl adipate and 10% tocopherol) | 5.0000 |
| Water, Purified | 68.000 |
| Hydroxyethylcellulose | 0.8000 |
| Phosphoric Acid | 0.3000 |
| Stearamidopropyl Dimethylamine | 1.0000 |
| Preservative premix (Butylene Glycol and Glycerin and Methylparaben and chlorphenesin | 3.8000 |
| Polysorbate 20 | 0.5000 |
| Glyceryl Stearate | 5.0000 |
| Glyceryl Dilaurate - neutralized | 5.0000 |
| Hydrogenated Polyisobutene | 2.0000 |
| Diisobutyl adipate | 5.0000 |
| PEG-60 Almond Triglyceride | 1.5000 |
| Glycerin and Bisabolol and Ginger Extract | 1.0000 |
| Neutrascent | 0.3000 |

Example 7: Medicated Anti-Blemish Nighttime Spot Treatment

Table 7 provides an exemplary medicated anti-blemish nighttime spot treatment formulation.

TABLE 7

Raw Material Description for Medicated Anti-Blemish Nighttime Spot Treatment Formulation

| | % |
|---|---|
| Gromwell root extract (2% $CO_2$ custom extraction product in 88% diisobutyl adipate and 10% tocopherol) | 2.5000 |
| Water, Purified | 44.790 |
| *Aloe Vera* Leaf powder | 0.0500 |
| Glycerin | 5.000 |
| Xanthan Gum | 0.4000 |
| Montmorillonite | 7.5000 |
| Dipotassium Glycyrrhizinate | 0.2000 |
| Disodium EDTA | 0.1000 |
| Allantoin | 0.2000 |
| Panthenol | 0.1000 |
| Unsaturated Lecithin [+Phospholipid] | 1.0000 |
| Vegetable Sorbitan Stearate | 1.0000 |
| BIS-PEG-18 Methyl Ether Dimethyl Silane | 3.0000 |
| Tocopheryl Acetate | 0.5000 |
| Emulsifying Wax NF | 2.0000 |
| Behenyl Alcohol | 1.5000 |
| Polysorbate 20 | 2.0000 |
| Hydrogenated Polyisobutene | 2.0000 |
| C12-C15Alkyl Benzoate | 4.0000 |
| Cetyl Dimethicone | 1.5000 |
| Glyceryl Dilaurate - neutralized | 1.5000 |
| PEG-60 Almond Glycerides | 1.0000 |
| Precipitated Sulfur | 5.0000 |
| Green Tea Extract (and) Butylene Glycol | 1.0000 |
| Glutathione | 0.1000 |
| Witch Hazel and Alcohol | 2.0000 |
| Water and Butylene Glycol and Cucumber (*Cucumis Sativus*) Fruit Extract and Sorbitol | 1.0000 |
| Butylene Glycol (and) Water (and) *Spiraea Ulmaria* Extract | 2.0000 |
| Liposomal Preparation with Licorice Embedment | 1.1600 |
| Glycerin and Water and Butylene Glycol and Ceramide 3 and Beta Sitosterol (Liposomal Preparation with Ceramide) | 1.9000 |
| Benzyl Alcohol | 0.5000 |
| PEG-60 Almond Glycerides | 1.0000 |
| Neutrascent | 0.3500 |
| Pentylene Glycol [Hydrolite 5] | 2.000 |
| Chlorphenesin | 0.1500 |

Example 8: Comparison of Various Formulations that Enhance or Reduce Gromwell Root's Propensity for Polymerization Chromatographic characterization of various formulations containing gromwell extracts: (A) 2% gromwell solubilized in 88% diisobutyl adipate with 10% tocopherol (B) anionic emulsion containing 0.10% gromwell processed under ambient conditions (C) cationic emulsion containing 0.10% gromwell processed at temperatures>180° F. High temperature processing induces undesirable napthoquinone adduct compounds which reduce solubility.

Figure 9:
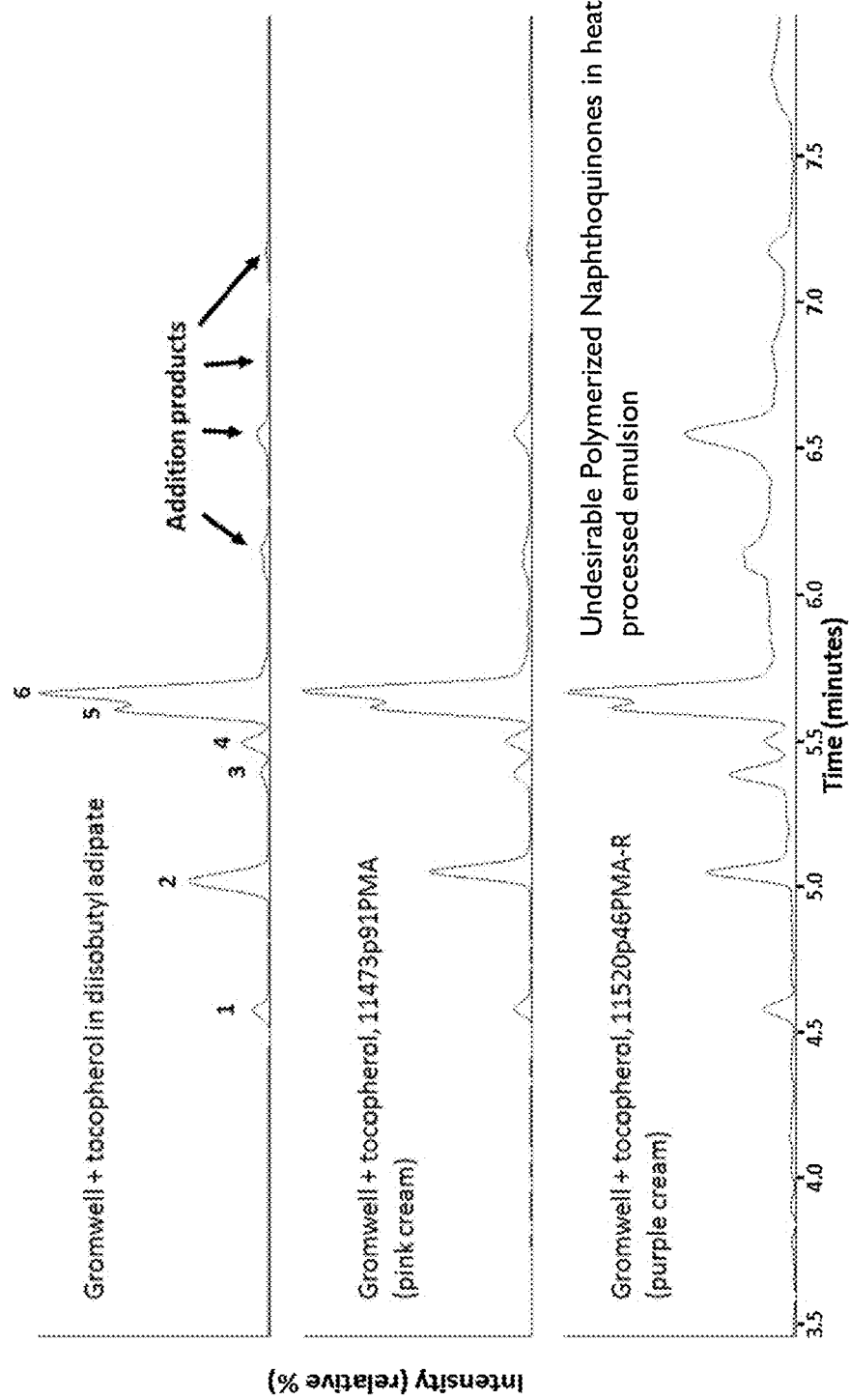
FIG. 9 depicts graphs comparing various formulations which enhance or reduce gromwell root's propensity for polymerization.

As shown in FIG. 9, various formulations enhance or reduce gromwell root's propensity for polymerization.

Example 9: Inhibition of SREBP1c Activity by Gromwell Root Extract

HEPG2 cell line was stably transfected with a luciferase reporter vector (pGL4.27) under the control of the full length human SREBP1c promoter, using Fugene 6 transfection reagent (Roche, Indianapolis, Ind.). Stable cells were grown and treated with extracts in a 96-well plate for 18 hr in 25 mM glucose DMEM medium to maximally stimulate SREBP1c promoter activity.

After 18 hrs of incubation, the medium from the cells was removed and the cells were washed once with 200 μl of phosphate buffered saline (PBS). Then 20 μl of passive lysis buffer (Biotium, Hayward, Calif.) was added per well and incubated at room temperature to lyse the cells. Subsequent to this, 100 µl of luciferin (Biotium, Hayward, Calif.) was added and the luminescence was read in a plate reader. Data are presented as percent inhibition relative to untreated cells which is set to 0%.

Gromwell root extract dose dependently repressed SREBP1c activity with an EC50=73 µg/mL.

Figure 14:
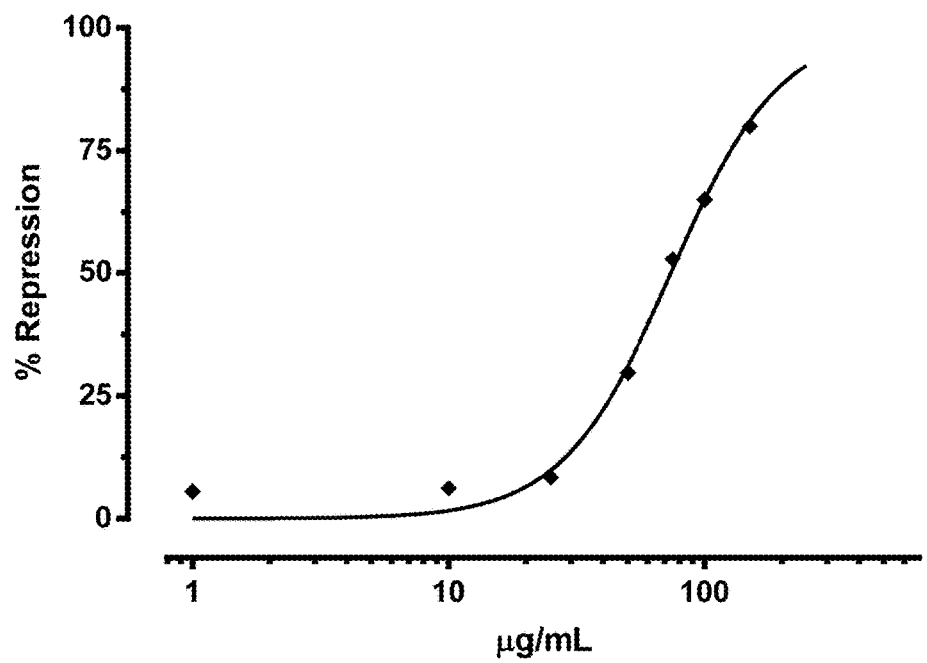
FIG. 14 depicts a graph demonstrating inhibition of SREBP1c activity by gromwell root.

As shown in FIG. 14, gromwell root extract would have 50% maximal efficacy at 0.0073% inclusion.

Example 10: Inhibition of SREBP1c Gene Expression and SCD1 by Gromwell Root Extract HepG2 cells were treated with Gromwell root extract for 18 h in 12-well plates. After 18 h, cells were washed with PBS and lysed. RNA was isolated from lysate with an RNA isolation kit from Qiagen. The qPCR reactions were carried with primers against SREBP1c and SCD1. Expression levels were calculated using double delta Ct analysis. Results were normalized to the housekeeping gene HPRT.

Figure 15:
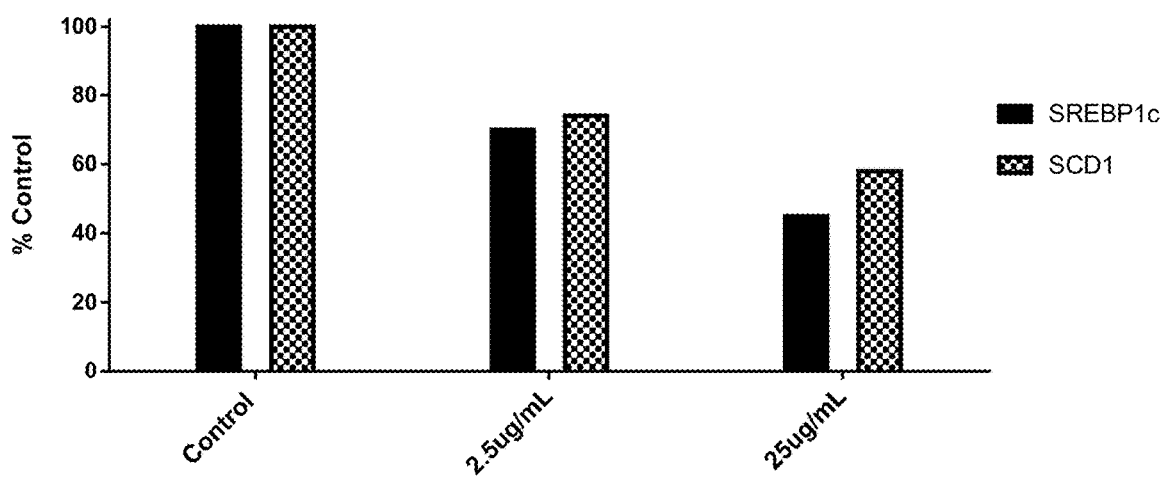
FIG. 15 depicts a bar graph demonstrating inhibition of gene expression of SREBP1c and SCD1 by gromwell root.

As illustrated in FIG. 15, gromwell root extract inhibited SREBP1c gene expression and SCD1, a target gene of SREBP1c.

Example 11: Gromwell Root Extract Reduces Sebum Production in SEB-1 Cells Stimulated with Insulin The immortalized human sebocyte cell line, SEB-1, was generated by transfecting cells with SV40 Large T antigen and maintained per published protocol (Thiboutot D, Jabara S, McAllister J, et al., "Human skin is a steroidogenic tissue: Steroidogenic enzymes and cofactors are expressed in epidermis, normal sebocytes, and an immortalized sebocyte cell line (SEB-1),"*J Invest Dermatol.* 120:905-14 (2003)). Lipid production was stimulated in SEB-1 cells by the addition of 1 uM insulin. Cells were treated with gromwell root extract (in the presence of 1 µM insulin) for 6 and 72 h. Lipid (i.e., sebum) production was detected by AdipoRed staining and quantified by using a fluorescent plate reader.

Figure 16:
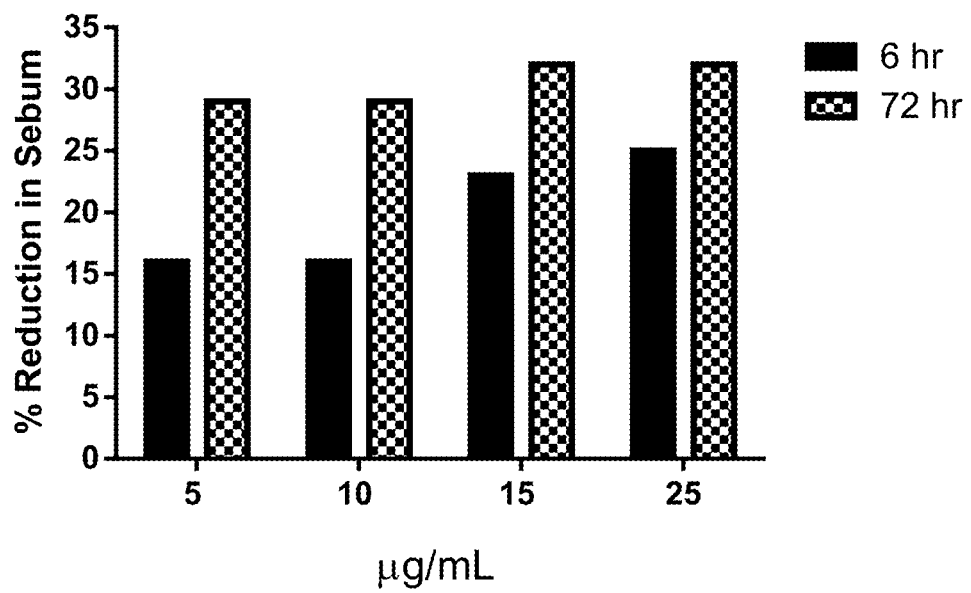
FIG. 16 depicts a bar graph demonstrating that gromwell root extract dose- and time-dependently reduced sebum production in SEB-1 cells stimulated with insulin.

As illustrated in FIG. 16, gromwell root extract dose- and time-dependently reduced sebum production in the immortalized human sebocyte cell line, SEB-1.

Example 12: Gromwell Root Extract Inhibition of Advanced Glycation End Products (AGEs)

Glycation refers to a series of non-enzymatic chemical reactions between proteins and sugars, which can occur both in-vitro and in-vivo. The earliest stages of glycation, also known as the Maillard reaction, are reversible. However, prolonged reactivity and/or rearrangement of the protein-sugar complex results in the formation of non-reversible Advanced Glycation Endproducts (AGEs). Glycated structures can have detrimental effects in-vivo due to the longevity of many proteins, and their role in diabetes and atherosclerosis has been extensively researched. Additionally, glycation events can negatively alter skin structure leading to reduced elasticity, loss of volume (under eye, cheeks and lips) impaired barrier function and discoloration. Glycation prevention promotes optimal health and aging, e.g., skin.

Bovine serum albumin (BSA) protein (5 mg/mL) was mixed with the sugar ribose (20 mg/mL). The resulting mixture was incubated, with and without treatment with gromwell root, in opaque 96-well plates for 48 hours in a 65° C. water bath. Following incubation, the plates were cooled to room temperature, centrifuged and the fluorescence of each well was measured with 340 nm excitation and 410 nm emission to detect the formation of glycation intermediates. Results were normalized to the known glycation inhibitor, aminoguanidine.

Figure 17:
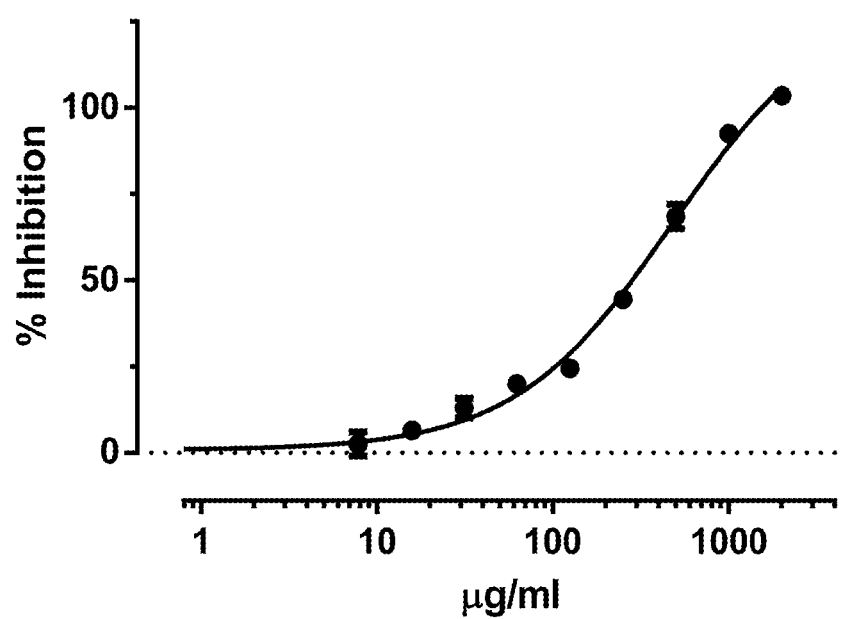
FIG. 17 depicts a graph showing inhibition of AGEs by gromwell root extract.

As shown in FIG. 17, gromwell root extract effectively inhibited the glycation reaction and inhibited AGEs.

Example 13: Contouring Lip and Cheek Jelly

Ambient emulsion prototype with "pink" payoff was prepared as follows

To prepare the Cheek Jelly with 0.01% to 0.10% gromwell extract, the following were placed in beaker with agitator under ambient conditions to form a water phase intermediate. Supplemental Red 6 or Red 7 Lake lipophilic agents can be directly charged to the main phase after emulsifier addition; or preblended to a separate oil phase vessel containing lipophilic agents. Variable concentrations of Red 6,7 and Yellow Lakes can influence the overall shade and/or payoff on the skin when combined with Gromwell,

TABLE 8

| Raw Material Description | | |
|---|---|---|
| | % | grams added |
| Water, Purified | 89.790 | 897.900 |
| Allantoin | 0.200 | 2.000 |
| Dipotassium glycyrrhizinate | 0.200 | 2.000 |
| Propanediol (Zemea) | 2.00 | 20.00 |
| Phenoxyethanol | 0.750 | 7.500 |
| Polyglyceryl-2 Triisostearate | 3.500 | 35.000 |
| Sodium Polyacrylate | 0.500 | 5.00 |
| Synthetic Fluorphlogopite and Titanium Dioxide [Timiron Synwhite 40] | 1.500 | 15.00 |
| Red 6 Lake Slurry [Kobo INBP50R6B] | 0.1000 | 1.00 |
| Red 7 Lake Slurry [Kobo INBP45R7B] | 0.100 | 1.00 |
| Polysorbate 80 | 1.000 | 10.00 |

In a separate suitably sized vessel, the following ingredients can be combined prior to addition to the main batch

TABLE 9

| Raw Material Description | | |
|---|---|---|
| | % | grams added |
| *Lithospermum Erythrorhizon* (Gromwell) Root $CO_2$ extraction 20% in *Simmondsia Chinensis* (Jojoba) Oil - FLAVEX | 0.0100 | 0.10 |
| *Arganica Spinosa* Kernel Oil [Argan] and tocopheryl Acetate and Bisabolol [Kobo SUNBOOST ATB] | 0.0274 | 0.27 |
| Tocopherol in Soybean Oil | 0.1006 | 1.01 |
| Isoamyl Acetate and Ethyl acetate and Linalyl Acetate and 3-Hexenol and Caprylic/Capric Triglyceride and Gamma-Undecalactone [SYMRISE 789404 PEACH INCI - CUSTOM: Lip Flavoring/Masking Blend] | 0.0220 | 0.22 |
| Triethyl citrate and Ethyl Vanillin and Heliotropine and Gamma Nonalactone and Anisaldehyde and Ethyl Hydroxypyrone and Benzaldehyde [SYMRISE 789412 - ALMOND VANILLA LIP INCI - Lip Flavoring/Masking Blend] | 0.200 | 2.00 |

Next, the following ingredients were carefully sprinkled to thicken the viscosity significantly:

TABLE 10

| | % | grams added |
|---|---|---|
| Sodium Polyacrylate | 0.650 | 6.50 |
| TOTAL | 100.000 | 1000.000 |

Next, the batch was moved to be milled and mixed for 5-10 minutes at 3600 RPM.

The mixing resulted in an ultra light weight, rapidly spreading gel masterbatch including a blend a natural and synthetic for a "fun" punch of pink to contour and hydrate lips/cheeks in a shade of coral candy.

The product was then placed in 5×4 oz jars for stability evaluation, 2×120 g for Micro-Initial, 1M/50'C, and remainder in 8-10 needle nose tubes.

The target specifications for physical properties were:
Viscosity: L9 (LVT, T Bar E, 6.0 rpm, 60 sec)>25,000 cP
Initial pH: L6 4.0-7.0
Specific Gravity (as is): L38, 0.990 or greater at 21° C.
A pearlescent, deep pink to coral viscous gel free of visible contamination
Finished Product Hazard Code: N-11

3 skin tissues were hydrated for 24 hrs. in 0.03% sodium azide solution. Next the skin tissues were immersed in Cheek Jelly (5 mL each vial) for 21 hours—equilibrium adsorption at ~skin surface temperature T=32° C. Next the skin tissues were transferred to placebo base collection reservoirs at 1, 4 and 36 hrs., T=32° C.: 1 hour reservoir base after skin tissue transfer [P4, P5, P6]; 4 hour reservoir base after skin tissue transfer [P7, P8, P9]; and 36 hour reservoir base after skin tissue transfer [P10, P11, P12].

Figure 18:
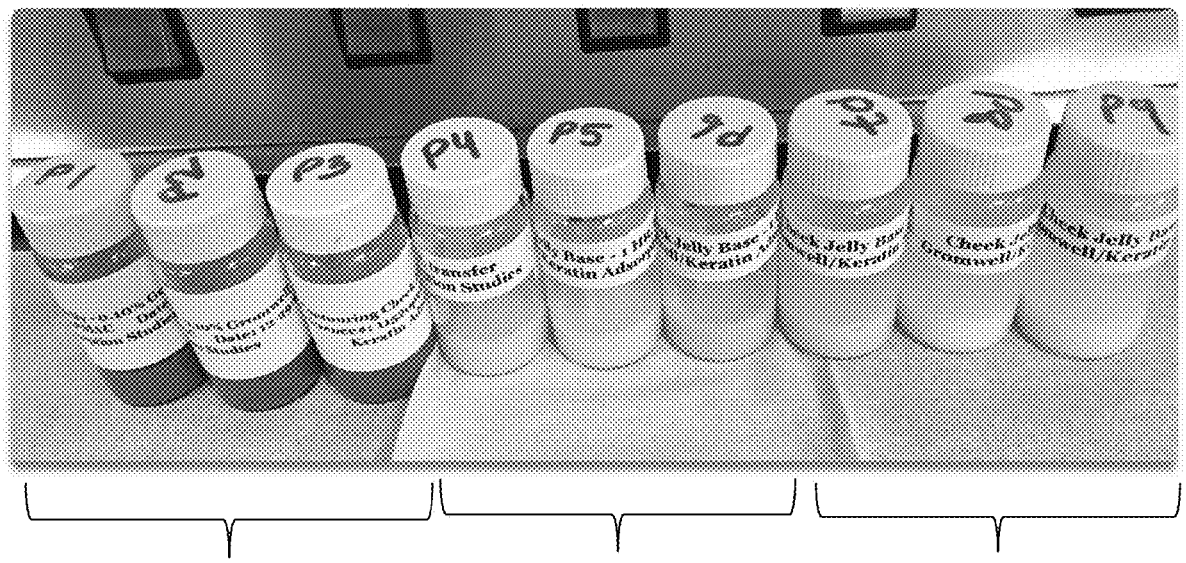
FIG. 18 shows skin tissues immersed in Cheek Jelly for 21 hrs.—equilibrium adsorption at ~skin surface temperature T=32° C., and skin tissues subsequently transferred to placebo base collection reservoirs at 1, 4 and 36 hrs.

FIG. 18 shows skin tissues immersed in Cheek Jelly for 21 hrs.—equilibrium adsorption at ~skin surface temperature T=32° C. [P1, P2, P3] and skin tissues subsequently transferred to placebo base collection reservoirs at 1, 4 and 36 hours as described above.

Figure 19:
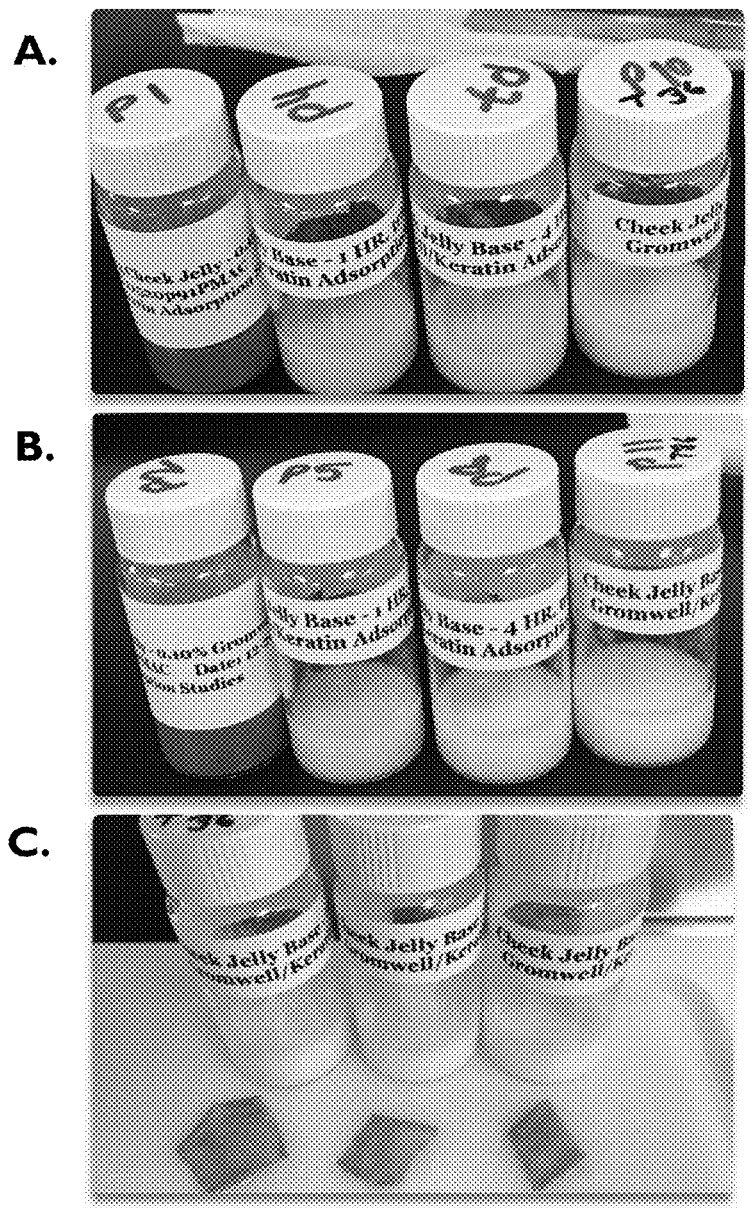
FIG. 19 shows photographs illustrating progression of skin adsorption.

FIG. 19 shows progression of skin adsorption: (A) and (B) for 21 hour skin saturation followed by 1 hr, 4 hr, 36 hr subsequent base transfer; and (C) reservoirs of skin immersed 36 hours in Cheek Jelly Base at T=32° C. FIG. 19 (A) shows reservoirs—21 hours skin immersion in cheek jelly prototype at 0.10% gromwell, followed by: 1 hr.=P4–5.45 g Base, 4 hr.=P7–5.10 g Base, and 36 hr.=P10–5.05 g Base. FIG. 19 (B) shows reservoirs—21 hr. skin immersion in cheek jelly prototype at 0.10% gromwell, followed by: 1 hr.=P5–5.15 g Base, 4 hr.=P8–5.04 g Base, and 36 hr.=P11–5.04 g Base. FIG. 19 (C) shows reservoirs of skin immersed 36 hours in Cheek Jelly Base at T=32° C.: 36 hr.=P10–5.05 g Base, P11–5.04 g Base, and P12–5.13 g Base (residual skin tissue original weight was 0.1065 g (P1), 0.0880 g (P2), 0.0858 g (P3)).

Figure 20:
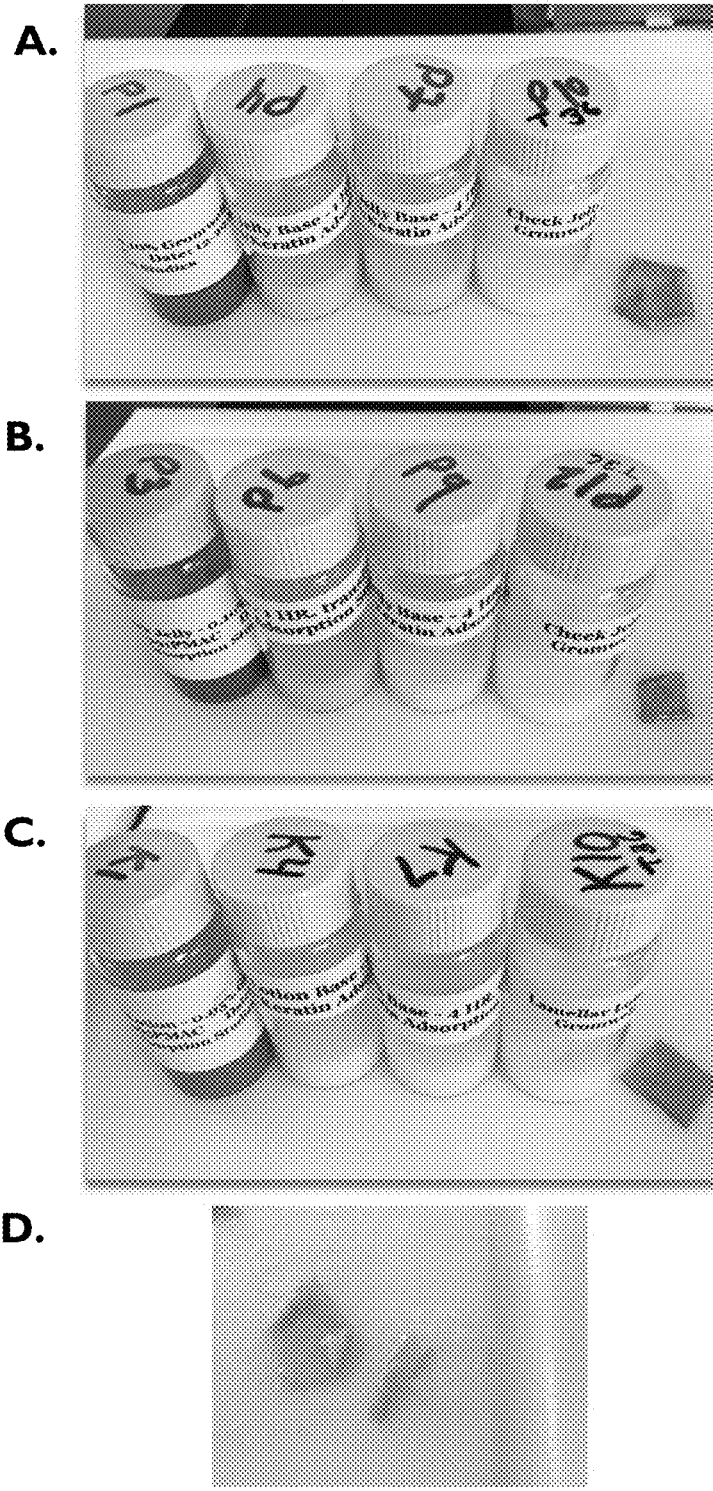
FIG. 20 shows photographs illustrating progression of skin adsorption for 21 hour skin saturation followed by 1 hr, 4 hr, 36 hr base transfer observation.

FIG. 20 shows progression of skin adsorption for 21 hour skin saturation followed by 1 hr, 4 hr, 36 hr base transfer: (A) residual skin tissue—visual skin adsorption of gromwell from coloration; and (B) residual skin tissue—visual skin adsorption of gromwell from coloration. A clean skin tissue reference is shown in FIG. 20 (D).

Figure 21:
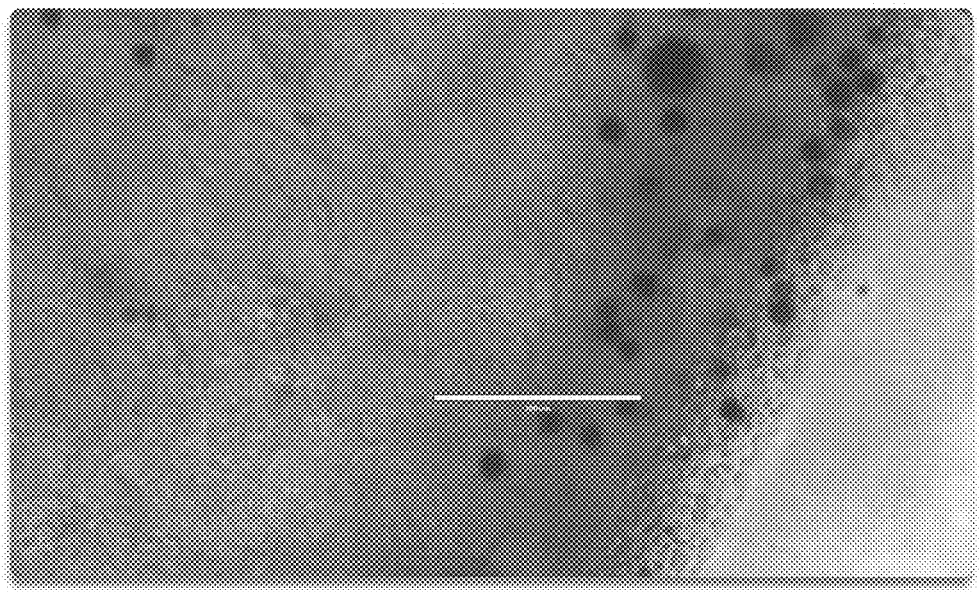
FIG. 21 shows skin tissue adsorption microscopy 36 hours after 21 hr. immersion in Cheek Jelly: (A) 40× magnification of P10 tissue; and (B) 10× magnification of P10 tissue.
Figure 21:
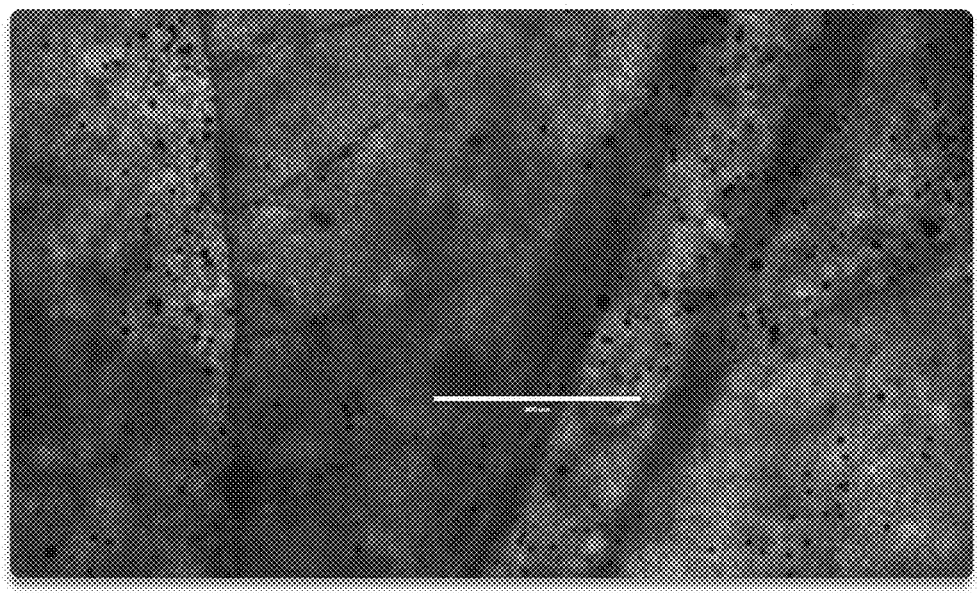

FIG. 21 shows skin tissue adsorption microscopy 36 hours after immersion in Cheek Jelly; (A) 40× magnification of P10 tissue; and (B) 10× magnification of P10 tissue.

Figure 22:
FIG. 22 depicts contouring lip and cheek jelly prototypes.

FIG. 22 depicts photographs of contouring lip and cheek jelly prototypes upon ambient shelf stability and elevated temperature exposures (favorable coloration).

Results of the tests using the Artistry Lip & Cheek Jelly ["Hint of Tint" Concept] with Natural Colorant—gromwell root are provided in Table 11 immediately below.

TABLE II

| Property | TEST METHOD | SPECS | CHECK POINT | | | | | | |
|---|---|---|---|---|---|---|---|---|---|
| | | | INITIAL | 1 M/ 25° C. | 1 M/ 50° C. | 3 M/ 25° C. | 3 M/ 40'C. | 6 M/ 25° C. | **6 M/ 40° C. |
| | | | Results | | | | | | |
| Microbio | M0030 | Passes/ Results, Total APC <500, Y&M <100 | Pass | Pass | Pass | Pass | Pass | Pass | Pass |
| pH | L0006A01 | 5.0-7.0 | 5.76 | 5.78 | 5.63 | 5.56 | 5.39 | 5.82 | 5.48 |
| Viscosity [cP] | L0009A0, LVT, TBar "E", 6.0 RPM, 60 Sec | >20,000 [cP] | 39390 | 38610 | 27300 | 39000 | 27940 | 33196 | 28830 |
| Appearance | Visual | A*** | sparkly, pearlescent pink to coral gel | A*** | A*** | A*** | A*** | A*** | A*** |
| Odor | Olfactory | A*** | fresh, tart scents of peach, citrus and vanilla | A*** | A*** | A*** | A*** | A*** | A*** |

**These accelerated stability results are predictive of a 3 year shelf life.
***A indicates "Acceptable"

FIG. 23 shows a photograph of gromwell lip & cheek jelly prototype at 6M at 40° C. exposure (L) as compared to 6M at 25° C. exposure (R).

Example 14: Anionic Lamellar Lotion with 0.05% Gromwell

An anionic lamellar lotion with similar emulsion microstructure to the Medicated Anti-Blemish Nighttime Treatment was prepared by stabilizing 0.05% Gromwell extract with the following exemplary formulation.

Table 12 includes an exemplary anionic lamellar lotion formulation.

TABLE 12

Raw Material Description for Anionic Lamellar Lotion Formulation

| | % |
|---|---|
| WATER PURIFIED | 70.9500 |
| Xanthan Gum | 0.4000 |
| Glycerin | 5.0000 |
| Dipotassium Glycyrrhizinate | 0.2000 |
| DISODIUM EDTA | 0.1000 |
| Unsaturated Lecithin [+Phospholipid] | 1.0000 |
| Vegetable Sorbitan Stearate | 1.0000 |
| BIS-PEG-18 Methyl Ether Dimethyl Silane | 3.0000 |
| Tocopheryl Acetate | 0.5000 |
| Behenyl Alcohol | 1.5000 |
| Polysorbate 20 | 2.0000 |
| Hydrogenated Polyisobutene | 2.0000 |
| C12-C15 Alkyl Benzoate | 4.0000 |
| Glyceryl Dilaurate - neutralized | 1.5000 |
| PEG-60 Almond Glycerides | 1.0000 |

TABLE 12-continued

Raw Material Description for Anionic Lamellar Lotion Formulation

| | % |
|---|---|
| Green Tea Extract (and) Butylene Glycol | 1.0000 |
| Symrise Neutrascent = Methyldihydrojasmonate & Tetramethyl Acetyloctahydronaphthalenes & Methylbenzyl Acetate & Hexyl Acetate & 3-Hexenol & Dimethyl Heptenal] | 0.2000 |
| Pentylene Glycol [Hydrolite 5] | 2.000 |
| Chlorphenesin | 0.150 |
| Gromwell Root $CO_2$ custom extraction 2% in Diisobutyl Adipate 88% & Tocopherol 10% | 2.50000 |

To test the anti-aging multipurpose facial lotion 3 skin tissues were hydrated for 24 hrs. in 0.03% Sodium azide solution. Next, the skin tissues were immersed in lotion (5 mL each vial) for 21 hrs.—equilibrium adsorption at ~skin surface temperature T=32° C. [K1, K2, K3]. Next, the skin tissues were transferred to placebo base collection reservoirs at 1, 4 and 36 hrs., T=32° C.; 1 hour samples are marked with K4, K5, K6, 4 hour samples are marked with K7, K8, K9; and 36 hour samples are marked with K10, K11, K12.

Referring to FIG. 20 (C), residual reservoirs and skin tissue for lamellar lotion experimentation are shown (K1=0.1286 g, K2=0.0848 g, K3=0.0458 g—original tissue weights). A clean skin tissue reference is shown in FIG. 20 (D).

Figure 24:
FIG. 24 depicts a photograph of prototypes of the gromwell facial mattifier.

FIG. 24 shows a photograph of the six month 40 C gromwell facial mattifier.

Testing results for Artistry Facial Mattifying Lotion with Natural Colorant—gromwell root are provided in the Table 13 below:

TABLE 13

| Property | TEST METHOD | SPECS | CHECK POINT | | | | | | |
|---|---|---|---|---|---|---|---|---|---|
| | | | INITIAL | 1 M/ 25° C. | 1 M/ 50° C. | 3 M/ 25° C. | 3 M/ 40° C. | 6 M/ 25° C. | **6 M/ 40° C. |
| | | | Results | | | | | | |
| Microbio | M0030 | Passes/Results, Total APC <500, Y&M <100 | Pass | Pass | Pass | Pass | Pass | Pass | Pass |
| Viscosity [cP] | L0009A00, LVT, TBar "E", 6.0 RPM, 60 Sec | >20,000 [cP] | 21060 | 20280 | 27300 | 22620 | 27940 | 21840 | 28830 |
| Appearance | Visual | ***A | sparkly, pearlescent pink to coral gel | ***A | ***A | ***A | ***A | ***A | ***A |
| Odor | Olfactory | ***A | fresh, tart scents of peach, citrus and vanilla | ***A | ***A | ***A | ***A | ***A | ***A |

**These accelerated stability results are predictive of a 3 year shelf life.

***A indicates "Acceptable"

Example 15: Anti-Aging Lip Gloss

Ambient process gelled oil to inhibitive skin glycation and provide barrier protection with a hint of pink coloration To prepare the Lip gloss with 0.01% to 0.10% gromwell extract, the following were placed in beaker with agitator under ambient conditions to form a gelled anhydrous oil with sustained moisture entrapment particularly for aging/thinning lips. Supplemental concentrations of Red 6,7 and Yellow Lakes can be added to influence the overall shade and/or payoff on the skin when combined with Gromwell,

TABLE 14

RAW MATERIAL DESCRIPTION for Anti-Aging Lip Gloss

| | % |
|---|---|
| Squalane (and) ethylene/propylene/styrene copolymer (and) butylene/ethylene/styrene copolymer (and) pentaerythrityl Tetra-di-t-butyl hydroxyhydrocinnamate [Versagel SQ] | 50.000 |
| Squalane | 21.350 |
| Fluorphlogopite [Synthetic Mica] | 3.000 |
| *Arganica Spinosa* Kernel Oil [Argan] and Tocopheryl Acetate and Bisabolol [Kobo SUNBOOST ATB] | 25.000 |
| *Lithospermum Erythrorhizon* (Gromwell Root) $CO_2$ extraction 20% in *Simmondsia Chinensis* (Jojoba) Oil and *Arganica Spinosa* Kernel Oil [Argan] and Tocopheryl Acetate and Bisabolol and Tocopherol and Soybean Oil | 0.4000 |
| Gamma-Undecalactone and *Ricinus Communis* (Castor) Seed Oil and Gamma-Nonalactone and Raspberry Ketone and Isoamyl Acetate and Ethyl Vanillin and 3-Hexenol [SYMRISE 789409 Coconut LIP INCI - CUSTOM: Lip Flavoring/Masking Blend] | 0.0500 |
| *Ricinus Communis* (Castor) Seed Oil and Isoamyl Acetate and Ethyl Vanillin and Linalyl Acetate and Raspberry Ketone and 3-Hexenol and Gamma-Undecalactone [SYMRISE 789402 Berry LIP INCI - CUSTOM: Lip Flavoring/Masking Blend] | 0.200 |
| TOTAL | 100.000 |

It is therefore intended that the foregoing detailed description be regarded as illustrative rather than limiting, and that it be understood that it is the following claims, including all equivalents, that are intended to define the spirit and scope of this invention.

The invention claimed is:

1. A topical composition consisting of:
 a. an active or an extract of the root of *Lithospermum erythrorhizon* in an amount ranging from about 0.05% to about 10.0% by weight of the total composition, and effective for treating or controlling an excessive oil production in skin and minimizing glycation in skin;
 b. a lipophilic solubilizer;
 c. a free radical stabilizer; and
 d. optionally, a pharmaceutically acceptable carrier.

2. The composition of claim 1, wherein the extract of the root of *Lithospermum erythrorhizon* comprises shikonin compound(s), and wherein the extract is standardized to 19-21% naphthoquinone.

3. The composition of claim 1, wherein the composition is a water-in-silicone emulsion.

4. The composition of claim 1, wherein the composition is an oil-in-water emulsion.

5. The composition of claim 1, wherein the lipophilic solubilizer is a non-comedogenic ester or natural oil.

6. The composition of claim 5, wherein the non-comedogenic ester is selected from the group consisting of adipates, caprylates, isononanoates, and select ethoxylated triglycerides.

7. The composition of claim 5, wherein the non-comedogenic ester is diisobutyl adipate.

8. The composition of claim 1, wherein the free radical stabilizer is a lipophilic antioxidant.

9. The composition of claim 8, wherein the lipophilic antioxidant is selected from the group consisting of tocotrienols, carotenoids, and phenolics.

10. The composition of claim 8, wherein the lipophilic antioxidant is tocopherol.

11. The composition of claim 1, wherein the composition is for suppressing sebum production in a subject with dermatosis.

12. The composition of claim 1, wherein the composition is for minimizing glycation in mature skin.

13. The composition of claim 1, wherein the composition has a pH from about 4.0 to about 8.0.

14. The composition of claim 1, wherein the composition is an oil-free composition.

15. The composition of claim 1, wherein the composition is in a form of cream, lotion, pack or powder, emulsion, liniment foam, plaster, granules, or ointment.

16. The composition of claim 1, wherein the composition is an over-the-counter cosmetic composition or a pharmaceutical composition.

17. The composition of claim 1, wherein the composition is a water-in-silicone emulsion, and wherein the active or the extract of the root of *Lithospermum erythrorhizon* (2% $CO_2$ extraction product in 88% diisobutyl adipate and 10% tocopherol) is in an amount ranging from about 0.5% to about 2% by weight of the composition.

18. The composition of claim 1, wherein the composition is a water-in-silicone emulsion, and wherein the active or the extract of the root of *Lithospermum erythrorhizon* (2% $CO_2$ extraction product in 88% diisobutyl adipate and 10% tocopherol) is in an amount ranging from about 2.5% to about 7.5% by weight of the composition.

19. The composition of claim 1, wherein the composition is an oil-in-water emulsion, and wherein the active or the extract of the root of *Lithospermum erythrorhizon* (2% $CO_2$ extraction product in 88% diisobutyl adipate and 10% tocopherol) is in an amount ranging from about 0.05% to about 1% by weight of the composition.

20. The composition of claim 1, wherein the composition is an oil-in-water emulsion, and wherein the active or the extract of the root of *Lithospermum erythrorhizon* (2% $CO_2$ extraction product in 88% diisobutyl adipate and 10% tocopherol) is in an amount ranging from 0.1% to about 5% by weight of the composition.

21. The composition of claim 1, wherein the composition is an oil-in-water emulsion, and wherein the active or the extract of the root of *Lithospermum erythrorhizon* (2% $CO_2$ extraction product in 88% diisobutyl adipate and 10% tocopherol) is in an amount ranging from about 2.5% to about 7.5% by weight of the composition.

22. The composition of claim 1, wherein the composition is an oil-in-water emulsion, and wherein the active or the extract of the root of *Lithospermum erythrorhizon* (2% $CO_2$ extraction product in 88% diisobutyl adipate and 10% tocopherol) is in an amount ranging from about 1.0% to about 5% by weight of the composition.

* * * * *